United States Patent [19]

Gries et al.

[11] Patent Number: 5,871,709
[45] Date of Patent: Feb. 16, 1999

[54] MACROCYCLIC COMPOUNDS AS COMPLEXING COMPOUNDS OR AGENTS, COMPLEXES OF METAL IONS THEREWITH AND USE THEREOF AS CONTRAST MEDIA FOR DIAGNOSTICS AND THERAPEUTICS

[75] Inventors: Heinz Gries; Hans-Joachim Weinmann; Johannes Platzek; Wolf-Rüdiger Press; Hubert Vogler, all of Berlin, Germany

[73] Assignee: Schering Aktiengesellschaft, Germany

[21] Appl. No.: 179,552

[22] Filed: Jan. 10, 1994

Related U.S. Application Data

[63] Continuation of Ser. No. 789,178, Nov. 8, 1991, Pat. No. 5,277,895.

[30]   Foreign Application Priority Data

Nov. 8, 1990 [DE] Germany ............... 40 35 760.0

[51] Int. Cl.$^6$ ............... A61K 51/04; A61B 5/055; C07D 225/00; C07F 5/00
[52] U.S. Cl. ............... 424/1.65; 424/9.361; 424/9.363; 540/465; 540/474; 540/475; 534/10; 534/14; 534/15; 534/16
[58] Field of Search ............... 534/10, 14, 15, 534/16; 540/465, 474, 475; 424/1.65, 9.363, 9.44, 9.361

[56]   References Cited

U.S. PATENT DOCUMENTS

| | | |
|---|---|---|
| 4,168,265 | 9/1979 | Tabushi et al. . |
| 4,174,319 | 11/1979 | Kobuke et al. . |
| 4,190,462 | 2/1980 | DeJong et al. . |
| 4,647,447 | 3/1987 | Gries et al. . |
| 4,678,667 | 7/1987 | Meares et al. . |
| 4,885,363 | 12/1989 | Tweedle et al. . |
| 5,049,667 | 9/1991 | Schaefer et al. . |
| 5,059,412 | 10/1991 | Simon et al. . |
| 5,132,409 | 7/1992 | Felder et al. . |
| 5,262,532 | 11/1993 | Tweedle et al. . |

FOREIGN PATENT DOCUMENTS

| | | |
|---|---|---|
| 232751 | 8/1987 | European Pat. Off. . |
| 299795 | 1/1989 | European Pat. Off. . |
| 305320 | 3/1989 | European Pat. Off. . |
| 365412 | 4/1990 | European Pat. Off. . |
| 434345 | 6/1991 | European Pat. Off. . |
| 434346 | 6/1991 | European Pat. Off. . |
| 3625417 | 2/1988 | Germany . |

OTHER PUBLICATIONS

Place et al., 5th Soc. Magnetic Resonance in Med. Mtg., Montreal, Canada, Aug. 1986.

*Primary Examiner*—Jose'G. Dees
*Assistant Examiner*—Michael G. Hartley
*Attorney, Agent, or Firm*—Millen, White, Zelano, & Branigan, P.C.

[57]   ABSTRACT

Tetraazacyclododecane compounds of general formula I $$\begin{array}{c} E \diagdown \diagup Q \\ N \quad N \\ \bigg[ \quad \quad \bigg], \\ N \quad N \\ E \diagup \diagdown E \end{array} \quad (I)$$

in which E and Q are defined herein and their salts with inorganic and/or organic bases, amino acids or amino acid amides are valuable pharmaceutical agents.

14 Claims, No Drawings

MACROCYCLIC COMPOUNDS AS COMPLEXING COMPOUNDS OR AGENTS, COMPLEXES OF METAL IONS THEREWITH AND USE THEREOF AS CONTRAST MEDIA FOR DIAGNOSTICS AND THERAPEUTICS

This is a Continuation of Ser. No. 07/789,178 filed Nov. 8, 1991, now U.S. Pat. No. 5,277,895 Jan. 11, 1994.

The invention relates to new mono-N-substituted 1,4,7, 10-tetraazacyclododecane derivatives, their complexes and complex salts, agents containing these compounds, their use in diagnosis as well as process for the production of these compounds and agents.

At the beginning of the fifties, metal complexes had already been considered as contrast media for radiology. But the compounds used at that time were so toxic that a use in humans was out of the question. It was therefore definitely surprising that certain complex salts proved sufficiently compatible so that a routine use in humans for diagnostic purposes could be taken into consideration. As first representatives of this family of substances, the dimeglumine salt of Gd DTPA (gadolinium(III) complex of diethylenetri-aminepentaacetic acid) described in the European patent with publication number 71564 and the meglumine salt of GD DOTA (gadolinium(III) complex of 1,4,7,10-tetracarboxymethyl-1,4,7,10-tetraazacyclododecane) described in French patent 2 539 996 have proven very successful (surprisingly) as contrast media for nuclear spin tomography. They have been registered under the names Magnevist(®) and Dotarem(®).

An important reason for their good usability in clinical practice lies in the high effectiveness in the case of the nuclear spin tomography, in particular in many brain tumors. Therefore their dosage, with 0.1 mmol/kg of body weight, can be very much lower than, for example, that of x-ray contrast media in many x-ray studies.

But there is now the wish to use chelates also in greater amounts. This is especially the case for detecting certain diseases outside the central nervous system with the help of nuclear spin tomography (NMR diagnosis), but quite especially in the use of chelates as x-ray contrast media.

In this connection, to keep the volume load of the body as low as possible, it is necessary to use highly concentrated chelate solutions. The previously known chelates are not very suitable in this respect above all because of their too high osmolality.

Therefore, there is a need for chelates that exhibit a smaller osmolality than the previously known chelates. At the same time, however, the requirements for the use of these compounds in humans relative to the difference between the effective and the toxic dose in animal study (the therapeutic range), the organ specificity, the stability, the contrast-enhancing action, the compatibility as well as the solubility of the complex compounds have to be met.

SUMMARY OF THE INVENTION

Thus, an object of the invention is to make these compounds and agents available as well as to provide a process for their production that is as simple as possible. This object and others are met by this invention.

The complex compounds according to the invention and the solutions prepared from them meet said requirements in a surprising way. They have a reduced osmolality as well as a more advantageous therapeutic range and/or stability and shelf life of the chemical components of the solution and/or organ specificity and/or compatibility (e.g., lower cardiovascular or allergy-type side effects) and above all a far better contrast-enhancing action than the previously usual diagnostic agents.

As evidence for the above-mentioned surprising and excellent properties of the compounds according to the invention, there can be pointed out the table at the end of the experimental part, in which the relaxivities $1/T_1$ (in plasma), usual as a measurement for the contrast-enhancing action of NMR contrast media, are compared, by way of example, with selected complexes according to the invention. The table indicates a marked superiority of these compounds in comparison with the NMR diagnostic agents Magnevist® and Dotarem® considered as prior art.

surprisingly, a large part of the complexes according to the invention shows a pharmacokinetic behavior other than Magnevist® and Dotarem®: after intravenous injection, Magnevist® and Dotarem® spread extracellularly and are excreted through the kidneys by glomerular secretion. A passage of intact cell membranes and an extrarenal elimination are practically not observed.

It has now been found that a large part of the compounds according to the invention surprisingly show both renal elimination and excretion with the feces after parenteral administration. But surprisingly, the elimination through the gallbladder is not the only extrarenal method of elimination: in NMR tests on rats, a contrast enhancement of the gastrointestinal tract was also observed unexpectedly after intravenous administration of the compounds according to the invention, i.e., these compounds are suitable both for the organ-specific NMR diagnosis of the hepatobiliary system and the stomach. The kidneys as well as implanted tumors are also contrasted.

The elimination (secretion) through the stomach has the advantage that a delimiting of the abdominal structures (e.g., pancreas) of the gastrointestinal tract is made possible with simultaneous contrast enhancement of pathological processes (tumors, inflammations). A representation of the renal system, the liver and the gallbladder and biliary tracts as well as the lymph nodes can, moreover, also be achieved. In addition to the improved representation of ulcers and stomach carcinomas, a study of the gastric juice secretion can also be performed with the help of the imaging processes.

Surprisingly, several of the complex compounds according to the invention are also resorbed after oral administration and then are eliminated by the hepatobiliary system, i.e., they are suitable also as oral liver contrast media.

By using the above-mentioned compounds—besides the diagnosis of the hepatobiliary system—thus patients suffering both from renal failures and gastrointestinal diseases (at least 10% of the population in the Western industrial countries) can be helped. Most of these patients and a large number of patients in whom the suspicion of such a disease is present, have to undergo diagnostic tests. At present, for gastrointestinal diseases, above all two methods suitable for this purpose are usual: endoscopy and x-ray diagnosis with the help of barium contrast media.

These tests have various drawbacks: they are affected by the risk of radiation exposure, causing trauma, connected with difficulties, occasionally even with risks, for the patients, and can therefore cause psychological stress. They have to be performed in most cases repeatedly, are relatively expensive to perform, require the active cooperation of the patients (e.g., taking a certain posture) and often cannot be used in the case of infirm and high-risk patients.

The object, to make available new diagnostic methods to detect and localize gastrointestinal diseases, which do not have these drawbacks, is therefore also achieved by the use of the above-mentioned complex compounds and agents.

Also, without specific measures, their pharmacokinetics make possible the improvement of the diagnoses of numerous diseases. The complexes are, for the most part, unchanged and quickly excreted again, so that in particular also in the case of the use of relatively toxic metal ions even of higher dosages, no harmful effects are observed.

The practical use of the new complexes is also facilitated by their advantageous chemical stability.

Another substantial advantage of the described complexes and complexing agents is their extraordinary chemical versatility. Besides the central atom, the properties can be matched to the requirements of effectiveness, pharmacokinetics, compatibility, solubility, manageability etc. by the selection of varied substituents on the macrocycle and/or of the salt formers. Thus, e.g., a very desirable specificity of the compounds can be achieved in diagnosis and treatment for structures in the organism, for certain biochemical substances, for metabolic processes, for conditions of the tissue or body fluids.

The macrocyclic compounds according to the invention are characterized by general formula I:

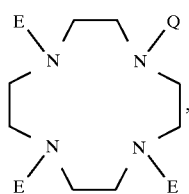

in which

E stands for a radical —CH($R^1$)—CO$_2$Y with Y meaning a hydrogen atom and/or a metal ion equivalent of an element of atomic numbers 21–29, 31, 32, 37–39, 42–44, 47, 49 or 57–83 and $R^1$ meaning a hydrogen atom, a branched or unbranched $C_1$–$C_{30}$ alkyl, $C_6$–$C_{10}$ aryl or $C_7$–$C_{30}$ aralkyl group, each optionally substituted with 1 to 6 hydroxy groups, Q stands for a radical —CH($R^1$)—CH(OH)R with R meaning a branched or unbranched $C_1$–$C_{30}$ alkyl or $C_7$–$C_{30}$ aralkyl radical, each containing 1 to 10 oxg atoms and optionally substituted by 1 to 6 hydroxy or OCOR$^2$ groups with $R^2$ meaning a hydrogen atom or a branched or unbranched $C_1$–$C_{30}$ alkyl, $C_6$–$C_{10}$ aryl or $C_7$–$C_{30}$ aralkyl radical, wherein R optionally contains 1 to 2 —OCO—groups, optionally 1 to 2 cyclohexane and/or cyclohexylene radicals (each of which can be substituted on their rings by 1 to 3 (CH$_2$)$_k$COOR$^2$ groups with k meaning the numbers 0 to 10), optionally 1 to 5 $C_1$–$C_7$ alkoxy, $C_6$–$C_{10}$ aryloxy or $C_7$–$C_{10}$ aralkyloxy groups, optionally a radical —NR$^2$—COR$^3$ or —CONR$^2$R$^3$, wherein R$^3$ has one of the meanings indicated for R$^2$, and/or 1 to 2 CO$_2$R$^2$ radicals, and wherein the aryl radicals optionally contained in the chain can be substituted by 1 to 3 branched or unbranched $C_1$–$C_{30}$-alkyl, $C_6$–$C_{10}$-aryl or $C_7$–$C_{30}$-aralkyl radicals, each optionally containing 1 to 5 oxygen (oxa) atoms, 1 to 3 hydroxy radicals, 1 to 5 $C_1$–$C_7$ alkoxy groups and/or 1 to 3 (CH$_2$)$_k$COOR$^2$ groups, and/or by 1 to 3 F, Cl, Br, OH, NO$_2$, NH$_2$, NCS, CO$_2$R$^2$, NHCOCH$_2$Cl, NHCOCH$_2$Br, NHCOCH$_2$R$^2$ or CON$_3$ radicals, and R' meaning a hydrogen atom or an R group, in which, if R' stands for a hydrogen atom, in the case of a 2-oxa-$C_1$–$C_{30}$ alkyl R chain, the latter—in addition to an optionally present, terminal methoxy or ethoxy group—has to be substituted by at least one of the above-indicated radicals, or Q stands for a second tetraazacyclododecane molecule bound by a bis(beta-hydroxy)-alkylene chain

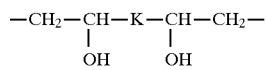

with K meaning a $C_1$–$C_{16}$ alkylene chain containing 1 to 6 oxygen (oxa) atoms and optionally substituted by 1 to 6 hydroxy, 1 to 6 hydroxy-$C_1$–$C_6$ alkyl and/or 1 to 8 $C_1$–$C_7$ alkoxy or $C_7$–$C_{10}$-aralkoxy groups and/or optionally containing 1 to 2 benzyloxy, phenylene, phenylenoxy and/or phenylenedioxy groups and their salts with inorganic and/or organic bases, amino acids or amino acid amides.

Compounds of general formula I with Y meaning hydrogen are called complexing agents and, with at least two of substituents Y meaning a metal ion equivalent, metal complexes.

If the agent according to the invention is intended for use in NMR diagnosis, the central ion of the complex salt has to be paramagnetic. These are in particular the divalent and trivalent ions of the elements of atomic numbers 21–29, 42, 44 and 58–70. Suitable ions are, for example, the chromium (III), manganese(II), iron(II), cobalt(II), nickel(II), copper (II), praseodymium(III), neodymium(III), samarium(III) and ytterbium(III) ion. Because of their very strong magnetic moment, the gadolinium(III), terbium(III), dysprosium(III), holmium(III), erbium(III) and iron(III) ion are especially preferred.

For the use of the agents according to the invention in nuclear medicine, the central ion has to be radioactive. For example, radioisotopes of elements copper, cobalt, gallium, germanium, yttrium, strontium, technetium, indium, ytterbium, gadolinium, samarium, silver, gold, rhenium and iridium are suitable.

If the agent according to the invention is intended for use in x-ray diagnosis, the central ion has to be derived from an element of a higher atomic number to achieve a sufficient absorption of the x rays. It has been found that diagnostic agents for this purpose, which contain a physiologically compatible complex salt with central ions of elements of atomic numbers between 21–29, 42, 44, 57–83, are suitable; these are, for example, the lanthanum(III) ion and the above-mentioned ions of the lanthanide series.

The alkyl, aryl and/or aralkyl radicals, optionally containing an aryl radical optionally standing for $R^1$ and $R^2$ or optionally contained in R as a substituent, contain 1 to 30 or $C_6$–$C_{10}$ or $C_7$–$C_{30}$ C atoms respectively and can be branched, unbranched, cyclic, saturated or unsaturated, which, in the case of $R^1$, optionally contains 1 to 6, preferably 1 to 3 hydroxy groups, in the case of R, optionally contains 1 to 5 oxygen atoms, 1 to 3 hydroxy radicals, 1 to 5, preferably 1 to 3 $C_1$–$C_7$ alkoxy groups and/or 1 to 3 (CH$_2$)$_k$COOR$^2$ groups with k meaning the numbers 0 to 10, preferably 0 to 5.

As preferred radicals, there can be mentioned by way of example: —CH$_3$, —C$_2$H$_5$, —i—C$_3$H$_7$, —C$_8$H$_{17}$, —C$_{15}$H$_{31}$, —C$_{16}$H$_{33}$, —C$_{17}$H$_{35}$, —CH$_2$OH, —CH$_2$CH$_2$OH, —CH(OH)CH$_2$OH, —C$_6$H$_5$, —CH$_2$C$_6$H$_5$, CH(OH)CH(OH)CH$_2$OH, —OCH$_3$, —OC$_2$H$_5$, —OCH$_2$C$_6$H$_5$, —OCH$_2$CH$_2$OCH$_3$, —OCH$_2$CH$_2$OCH$_2$CH$_2$OH, —(CH$_2$)$_5$OH, —CH$_2$CO$_2$H, —(CH$_2$)$_2$CO$_2$H, —OCH$_2$CO$_2$H, —O(CH$_2$)$_5$CO$_2$H, —CH$_2$CO$_2$C$_2$H$_5$, —CH$_2$CO$_2$iC$_3$H$_7$, —CH$_2$—O—CH(CO$_2$H)—CH$_2$CO$_2$H, —O—CH$_2$—CH(OCH$_3$)—CH$_2$—OCH$_3$.

$R^1$ and R' each preferably stand for a hydrogen atom.

R stands for a branched, unbranched, saturated or unsaturated $C_1$–$C_{30}$, preferably for a $C_1$–$C_{20}$ alkyl or $C_7$–$C_{30}$ aralkyl radical, which is interrupted by 1 to 10, preferably 1 to 5 oxygen atoms and is optionally substituted by 1 to 6, preferably 1 to 3 hydroxy or $OCOR^2$ groups. It can contain 1 to 2 cyclohexane and/or cyclohexylene radicals, which on their part can be substituted by 1 to 3, preferably 1 $(CH_2)_k COOR^2$ groups.

Further, the $C_1$–$C_{30}$ radical standing for R can be substituted by 1 to 5, preferably 1 to 3 $C_1$–$C_7$ alkoxy, $C_6$–$C_{10}$ aryloxy or $C_7$–$C_{10}$ aralkoxy groups (such as, e.g., $OCH_3$, $OC_2H_5$, $OCH_2C_6H_5$, $OC_6H_5$), a radical -$NR^2COR^3$ (such as, e.g., $NHCOC_6H_5$, $NCH_3COCH_3$, $NHCOC_2H_5$, $NCH_3COCH_2C_6H_5$), a radical —$CONR^2R^3$ (such as, e.g., $CONHCH_3$, $CONHC_6H_5$, $CONCH_3C_6H_5$, $CONH_2$, $CONHC_3H_7$) and/or 1 to 2 —$CO_2R^2$ radicals (such as, e.g., $CO_2CH_3$, $CO_2C_2H_5$, $CO_2{}^iPr$, $CO_2{}^tBut$, $CO_2CH_2C_6H_5$). The 1 to 3, preferably 1 aryl radical or radicals optionally contained in this chain can be substituted by 1 to 3, preferably 1 to 2 of the $C_1$–$C_{10}$ alkyl, aryl and/or aralkyl chains described in more detail above, and/or by 1 to 3, preferably 1 to 2 F, Cl, Br, OH, $NO_2$, $NH_2$, NCS, $CO_2R^2$, $NHCOCH_2Cl$, $NHCOCH_2Br$, $NHCOCH_2R$, $CON_3$ radicals.

As preferred radicals R, there can be mentioned by way of example:

—$CH_2$—O—$C_6H_5$, —$CH_2$—O—$CH_2C_6H_5$, —$CH_2$—O—$C_{10}H_{20}$—OH, —$CH_2$—O—$C_{10}H_{20}$—COOH, —$CH_2$—O—$C_5H_{10}$—COOH, —$CH_2CH_2$—$(C_7H_{14})$—$OCH_3$, —$CH_2$—$CH_2$—$CH_2$—$CH_2$—O—$CH_2$—COOH, —$CH_2$—O—$C_6H_{10}$—O—$CO_2H$, —$CH_2$—O—$C_6H_{10}$—OH, —$C_6H_{12}$—O—$CH_2$—COOH, —$CH_2$—O—$C_5H_{10}NHCOC_6H_5$, —$CH_2$—O—$C_2H_5$, $NHCOC_6H_5$, —$CH_2$—O—$C_2H_5CONH$—$C_3H_7$, —$CH_2$—O—$CH_2CH_2$—O—$CH_2CH_2$—O—$C_5H_{11}$, —$CH_2$—O—$CH_2$—CH(OH)$CH_2$OH, $CH_2$—O—$C_6H_4NCS$, —$CH_2$—O—$C_6H_4OCH_3$, —$CH_2$—O—$CH_2CH_2CH_2C_6H_4OCH_3$, —$CH_2$—O—$C_6H_4$—Cl, —$CH_2O$—$C_6H_4$—$C_5H_{10}$—OH, —$CH_2$—O—$C_6H_3(CH_3)_2$, —$CH_2$—O—$C_6H_4(CH_2)_2$—COOH, —$CH_2$—O—$C_6H_4$—$OCH_2COOH$, —$CH_2$—O—$C_6H_4COOH$, —$CH_2O$—$CH_2$—$C_6H_4COOH$, —$CH_2O$—$C_6H_4CH_2COOH$, —$CH_2O$—$C_6H_4CH_2COOC_2H_5$, —$(CH_2)_9$—O—$CH_2$—$C_6H_5$, —$CH_2$—OCO—$CH_{15}H_{31}$, $(CH_2)_9$—$OCH_3$, —$CH_2$—O—$C_9H_{18}$—O—$CH_2C_6H_5$, —$CH_2$—O—$C_9H_{18}OH$, —$C_8H_{16}$—$(CH_2$—O—$CH_2$—$C_6H_5)$—$C_2H_5$, —$C_9H_{18}$—O—$C_6H_4$—O—$CH_2$—$C_6H_5$, —$C_9H_{18}$—O—$C_6H_4$—OH, —$(CH_2)_9$—O—$CH_2$—$C_6H_4$—$CH_2COOH$, —$(CH_2)_9$—O—$C_{10}H_{20}$—OH, —$(CH_2)_9$—O—$C_5H_{10}$—COOH, —$(CH_2)_9$—$OCOCH_3$, —$(CH_2)_9$—O—$COC_4H_9$, —$(CH_2)_9$—$OCOC_2H_4COOH$, —$(CH_2)_9$—$OCOC_6H_4COOH$, —$(CH_2)_9$—$OCOC_6H_{10}OCOOH$.

Dimers, i.e. compounds of general formula I, in which Q stands for a second tetraazacyclododecane molecule bound by a bis(beta-hydroxy)-alkylene chain

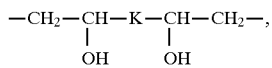

also belong to the compounds according to the invention. The number of oxygen atoms contained in $C_1$–$C_{16}$, preferably $C_1$–$C_{10}$ alkylene chain K is preferably 1 to 3. It optionally contains 1 to 6 hydroxy and/or 1 to 6 hydroxy-$C_1$–$C_6$ alkyl groups and/or 1 to 8, preferably 1 to 2 $C_1$–$C_7$ alkoxy, aryloxy and/or aralkoxy groups.

As preferred alkylene chain K, there can be mentioned by way of example:

—$CH_2$—O—$CH_2$—, —$CH_2O$—$CH_2CH_2$—O—$CH_2$—, —$CH_2$—O—$C_3H_6$—O—$CH_2$—, —$CH_2$—O—$C_4H_8$—O—$CH_2$—, —$CH_2O$—$CH(CH_2OH)$—$CH_2$—$CH(CH_2OH)$—O—$CH_2$—, —$CH_2O$—$CH_2$—CH(OH)—$CH_2$—O—$CH_2$—, —$CH_2$—O—$CH_2$—CH($OCH_3$) $CH_2$—O—$CH_2$—, —$CH_2$—$OCH_2$—C($CH_2OH)_2$—$CH_2$—O—$CH_2$—, $CH_2$—O—$C_6H_4$—O—$CH_2$—, —$CH_2$—O—$CH_2$—$C_6H_4$—$CH_2$—O—$CH_2$—, —$CH_2$—O—$CH_2$—CH(OH)—CH(OH)—$CH_2$—O—$CH_2$—, —$CH_2$—O—$CH_2$—CH($CH_2OH$) —$CH_2$—O—$CH_2$—, —$CH_2$—O—$C_6H_4$—O—$C_6H_4$—O—$CH_2$—.

The residual acidic hydrogen atoms, i.e., those which have not been substituted by the central ion, can optionally be substituted completely or partially by cations of inorganic and/or organic bases, amino acids or amino acid amides.

Suitable inorganic cations are, for example, the lithium ion, the potassium ion, the calcium ion, the magnesium ion and in particular the sodium ion. Suitable cations of organic bases are, among others, those of primary, secondary or tertiary amines, such as, for example, ethanolamine, diethanolamine, morpholine, glucamine, N,N-dimethylglucamine and in particular N-methylglucamine. Suitable cations of amino acids are, for example, those of lysine, arginine, and ornithine, as well as the amides of otherwise acid or neutral amino acids such as, e.g., lysine methyl amide, glycine ethyl amide and serine methyl amide.

The production of the tetraazacyclododecane compounds, according to the invention, of general formula I, takes place in that, in a way known in the art, compounds of general formula II

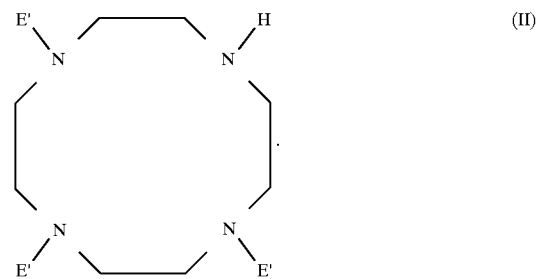

in which

E' means the radical indicated for E, in which hydroxy groups optionally present in it are optionally protected, are reacted with a feedstock of general formula III or IV

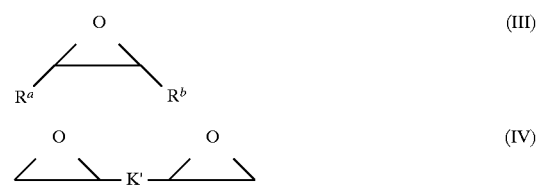

in which

K' means the radical indicated for K, in which hydroxy groups optionally present in it are optionally protected, $R^a$ and $R^b$ have the meaning indicated for R' and R, but contain no groups $NH_2$, NCS, $NHCOCH_2Cl$ or $NHCOCH_2Br$ and optionally present carboxyl groups are optionally present in protected form, in water or in water-miscible solvents, such as, e.g., acetonitrile, DMF, DMA, ethanol, methanol, dioxane, THF, DMSO, DME or their mixtures at temperatures of 0° C. to 170° C., preferably 20° to 100° C., within 12 to 48 hours, preferably 12 to 24 hours, while adding inorganic and/or organic bases, such as, e.g., potassium, sodium, lithium, calcium, barium, magnesium hydroxide, sodium carbonate, potassium carbonate, triethylamine, tripropylamine, tributylamine, pyridine, DMAP, Reillex®, Triton B®, optionally still present protective groups are cleaved, the thus obtained complexing agents (Y stands for hydrogen atoms) are reacted with at least one metal oxide or metal salt of an element of atomic numbers 21–29, 31, 32, 37–39, 42–44, 47, 49 or 57–83 and then—if desired—present acidic hydrogen atoms are substituted by cations of inorganic and/or organic bases, amino acids or amino acid amides, and—if the desired end products are to contain the groups $NH_2$, NCS, $NHCOCH_2Cl$, $NHCOCH_2Br$ or $CON_3$—a start is made from feedstocks of general formula III, which, instead of these groups, contain $NO_2$ or $CO_2R^2$ groups, then the last-mentioned groups are converted to the above-mentioned, desired functional groups, and this conversion can take place before or after the complexing of the complexing agents and subsequent substitution of optionally still present acidic hydrogen atoms with the respectively desired metal ions.

As hydroxy protecting groups, all those are suitable which can be easily introduced and later can also be easily cleaved again with reformation of the finally desired free hydroxy group. Preferred protective groups are ether groups, such as, for example, the benzyl, 4-methoxybenzyl, 4-nitrobenzyl, trityl, diphenylmethyl, triphenylmethyl, trimethylsilyl, dimethyl-t-butylsilyl, diphenyl-t-butylsilyl group. But the hydroxy groups in the form of ketals protected with, for example, acetone, acetaldehyde, cyclohexanone or benzaldehyde, are preferred.

The cleavage of the hydroxy protecting groups takes place in a way known in the art, for example, in the case of a benzyl ether, by reductive cleavage with lithium/ammonia or by hydrogenolytic cleavage in the presence of, for example, palladium-carbon and, in the case of an ether or ketal cleavage, by acid treatment with the help of, for example, cation exchangers, trifluoroacetic acid or mineral acids [see, e.g., T. W. Greene, "Protective Groups in Organic Synthesis," John Wiley and Sons (1981).

As acid protecting groups, lower alkyl, aryl and aralkyl groups, for example, the methyl, ethyl, propyl, n-butyl, t-butyl, phenyl, benzyl, diphenylmethyl, triphenylmethyl, bis(p-nitrophenyl)-methyl group, as well as trialkylsilyl groups, are suitable.

The cleavage of the acid protecting groups takes place according to the processes known to one skilled in the art, for example, by hydrolysis, hydrogenolysis, alkaline saponification of the esters with alkali in aqueous alcoholic solution at temperatures of 0° to 50° C., acid saponification with mineral acids or in the case of, e.g., tert-butyl esters, with the help of trifluoroacetic acid.

In the reaction of the trisubstituted tetraazacyclododecane derivatives II, known, e.g., from European patent applications EP 255 471 and EP 287 465, with epoxides III, the reaction is performed with a 1.05 to 5 times, preferably 1.05 to 3 times, excess of III.

In contrast, in the synthesis of dimeric macrocycles the reaction is performed with 0.1 to 0.49 equivalents of IV.

The thus obtained complexing agents are isolated after purification on silica gel columns, reversed-phase columns (RP-18) or on ion-exchange columns (e.g., IRA 67, IR 120, AMB 252).

The functional groups $NH_2$, $NHCOCH_2Cl$, $NHCOCH_2Br$ and NCS, optionally desired in the end product, are generated after the alkylation with an epoxide III containing an $NO_2$ group (either before or after the optionally desired introduction of metal in the macrocycle) according to methods known in the literature (European patent application publication no.: 292 689; U.S. Pat. No. 4,678,667; Bioconjugate Chem. 1990, 1, 59; J. Med. Chem. 1989, 32, 236).

Epoxides III and IV, required as feedstocks, are known or can be produced analogously to methods known in the literature, e.g., by reaction of alcohols with epichlorohydrin (Synthesis 1983, 117; Houben-Weyl, Methoden der Organischen Chemie [Methods of Organic Chemistry], Volume 613, Georg-Thieme-Verlag Stuttgart, 1965) and epoxidation of substituted allyl alcohols or unsaturated ethers [J. Org. Chem. 35, 215 (1970), Houben-Weyl, Georg Thieme-Verlag Stuttgart 1965; Tetrahedron Lett. 1965, 849].

The production of the metal complexes according to the invention takes place in the way as disclosed in German laid-open specification 34 01 052, by the metal oxide or a metal salt (for example, nitrate, acetate, carbonate, chloride or sulfate of the element of atomic numbers 21–29, 31, 32, 37–39, 42–44, 47, 49, 57–83) being dissolved or suspended in water and/or a lower alcohol (such as, methanol, ethanol or isopropanol) and reacted with the solution or suspension of the equivalent amount of complexing ligands and then, if desired, present acidic hydrogen atoms being substituted by cations of inorganic and/or organic bases or amino acids.

The introduction of the desired metal ions can take place in this case both before and after the cleavage of the hydroxy protecting groups.

The neutralization of optionally still present free carboxy groups takes place with the help of inorganic bases (for example, hydroxides, carbonates or bicarbonates) of, for example, sodium, potassium, lithium, magnesium or calcium and/or organic bases, such as, among others, primary, secondary and tertiary amines, such as, for example, ethanolamine, morpholine, glucamine, N-methylglucamine and N,N-dimethylglucamine, as well as basic amino acids, such as, for example, lysine, arginine and ornithine or amides of originally neutral or acid amino acids.

For the production of neutral complex compounds, so much of the desired bases can be added, for example, to the acid complex salts in aqueous solution or suspension that the neutral point is reached. The obtained solution can then be evaporated to dryness in a vacuum. Often, it is advantageous to precipitate the formed neutral salts by adding water-miscible solvents, such as, for example, lower alcohols (methanol, ethanol, isopropanol and others), lower ketones (acetone and others), polar ethers (tetrahydrofuran, dioxane, 1,2-dimethoxyethane and others) and thus to obtain crystallizates that are easy to isolate and easy to purify. It has proven especially advantageous to add the desired base as early as during the complexing of the reaction mixture and thus to save a process step.

Another possibility, to achieve neutral complex compounds, consists in converting the remaining acid groups in the complex completely or partially to, for example, esters or amides. This can take place on the finished complex by later reaction (e.g., by exhaustive reaction of the free carboxy groups with dimethyl sulfate).

The production of the pharmaceutical agents according to the invention takes place also in a way known in the art, by the complex compounds according to the invention—optionally while adding the additives usual in galenicals—being suspended or dissolved in aqueous medium and then the suspension or solution optionally being sterilized. Suitable additives are, for example, physiologically harmless buffers (such as, for example, tromethamine), additives of complexing agents (such as, for example, diethylenetriaminepentaacetic acid) or—if necessary—electrolytes, such as, for example, sodium chloride or—if necessary—antioxidants, such as, for example, ascorbic acid.

If suspensions or solutions of the agents according to the invention in water or physiological salt solution are desired for enteral administration or other purposes, they are mixed with one or more auxiliary agents usual in galenicals (for example, methyl cellulose, lactose, mannitol) and/or surfactants (for example, lecithins, Tween®, Myrj®) and/or aromatic substance(s) for taste correction (for example, essential oils).

In principle, it is also possible to produce the pharmaceutical agents according to the invention also without isolating the complex salts. In each case, special care has to be taken to carry out the chelation so that the salts and salt solutions according to the invention are practically free of noncomplexed toxically acting metal ions.

This can be assured, for example, with the help of color indicators, such as xylenol orange, by control filtrations during the production process. The invention therefore relates also to the process for the production of complex compounds and their salts. As a final safety measure, there remains a purification of the isolated complex salt.

The pharmaceutical agents according to the invention preferably contain 0.1 micromol–3 mol/l of the complex salt and are generally added in amounts of 0.1 micromol–5 mmol/kg. They are intended for enteral and parenteral administration. The complex compounds according to the invention are used:

1. for NMR and x-ray diagnosis in the form of their complexes with the ions of the elements with atomic numbers 21–29, 42, 44 and 57–83;
2. for radiodiagnosis and radiotherapy in the form of their complexes with the radioisotopes of the elements with atomic numbers 21, 26, 27, 29, 31, 32, 37–39, 43, 47, 49, 62–64, 67, 70, 71, 75, 77, 79 and 83.

The agents according to the invention meet the varied requirements for suitability as contrast media for nuclear spin tomography. Thus, they are excellently suited for this purpose, to improve the image, obtained with the help of nuclear spin tomograph, in its informative value after enteral or parenteral administration by increasing the signal intensity. Further, they show the high effectiveness, which is necessary to load the body with as low as possible amounts of foreign substances, and the good compatibility, which is necessary to maintain the noninvasive character of the studies.

The good water solubility and low osmolality of the agents according to the invention makes it possible to produce highly concentrated solutions, thus to keep the volume load of the circulatory system within justifiable limits and to compensate for the dilution by the body fluid, i.e., NMR diagnostic agents have to be 100 to 1000 times more water-soluble than for NMR spectroscopy. Further, the agents according to the invention not only exhibit a high stability in vitro, but also a surprisingly high stability in vivo, so that a release or an exchange of the ions that are not covalently bound—toxic in themselves—in the complexes takes place only exceptionally slowly within the time in which the new contrast media are again completely excreted.

In general, the agents according to the invention for use as NMR diagnostic agents are added in amounts of 0.0001–5 mmol/kg, preferably 0.005–0.5 mmol/kg. Details of use are discussed, for example, in H. J. Weinmann et al., Am. J. of Roentgenology 142, 619 (1984).

Further, the complex compounds according to the invention can be used advantageously as susceptibility reagents and as shift reagents for the in vivo NMR spectroscopy.

The agents according to the invention are also suitable as radiodiagnostic agents because of their advantageous radioactive properties and the good stability of the complex compounds contained in them. Details of their use and dosages are described, e.g., in "Radiotracers for Medical Applications," CRC Press, Boca Raton, Florida.

Another imaging method with radioisotopes is the positron emission tomography, which uses positron-emitting isotopes, such as, e.g., $^{43}$Sc, $^{44}$Sc, $^{52}$Fe, $^{55}$Co and $^{68}$Ga (Heiss, W. D.; Phelps, M. E.; Positron Emission Tomography of Brain, Springer Verlag Berlin, Heidelberg, N.Y. 1983).

The compounds according to the invention can also be used in radioimmunotherapy or radiation therapy. These are distinguished from the corresponding diagnosis only by the amount and type of the isotope used. In this case, the purpose is the destruction of tumor cells by high-energy shortwave radiation with as low as possible a range of action. Suitable beta-emitting ions are, for example, $^{46}$Sc, $^{47}$Sc, $^{48}$Sc, $^{72}$Ga, $^{73}$Ga and $^{90}$Y. Alpha-emitting ions exhibiting suitably low half-lives are, for example $^{211}$Bi, $^{212}$Bi, $^{213}$Bi and $^{214}$Bi, and $^{212}$Bi is preferred. A suitable photon- and electron-emitting ion is $^{158}$Gd, which can be obtained from $^{157}$Gd by neutron capture.

If the agent according to the invention is intended for use in the variant of radiation therapy proposed by R. L. Mills et al. [Nature Vol. 336, (1988), p. 787], the central ion has to be derived from a Mossbauer isotope, such as, for example, $^{57}$Fe or $^{151}$Eu.

In the case of the in vivo administration of the therapeutic agents according to the invention, they can be administered together with a suitable vehicle, such as, for example, serum or physiological common salt solution, and together with another protein, such as, for example, human serum albumin. The dosage, in this case, is a function of the type of cellular disturbance, the metal ion used and the type of method, e.g., brachytherapy.

The therapeutic agents according to the invention are administered parenterally.

Details of the use of radiotherapeutic agents are discussed, e.g., in R. W. Kozak et al., TIBTEC, October 1986, 262.

The agents according to the invention are excellently suited as x-ray contrast media, and it is especially to be emphasized that no signs of the anaphylactic-type reactions in biochemical-pharmacological studies known from contrast media containing iodine can be discerned with them. They are especially valuable because of the advantageous absorption properties in the ranges of higher tube voltages for digital subtraction techniques.

In general, the agents according to the invention for use as x-ray contrast media are added analogously to, for example, meglumine diatrizoate in amounts of 0.1–5 mmol/kg, preferably 0.25–1 mmol/kg.

Details of the use of x-ray contrast media are discussed, for example, in Barke, Roentgenkontrastmittel [X-Ray Contrast Media], G. Thieme, Leipzig (1970) and P. Thurn, E. Buecheler—"Einfuhrung in die Roentgendiagnostik" ["Introduction to X-Ray Diagnosis"], G. Thieme, Stuttgart, N.Y. (1977).

Altogether, it has been possible to synthesize new complexing agents, metal complexes and metal complex salts, which open up new possibilities in diagnostic and therapeutic medicine. Above all, the development of new type imaging processes in medical diagnosis makes this development appear desirable.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German P 40 35 760.0, filed Nov. 8, 1990, are hereby incorporated by reference.

EXAMPLES

Example 1 a) 1,1'-(2,9-Dihydroxy-4,7-dioxa-1,10-decyl)-bis-[(4,7,10-tris-carboxymethyl)-l,4,7,10-tetraazacyclododecane]

17.9 g (51.67 mmol) of 1,4,7-triscarboxymethyl-1,4,7,10-tetraazacyclododecane (DO3A) is dissolved in 80 ml of water and the pH is adjusted to 13 with 5n sodium hydroxide solution. Then, a solution of 3 g (17.22 mmol) of 1,2-9,10-diepoxy-4,7-dioxadecane in 30 ml of dioxane is instilled within one hour and stirred at 50° C. for 24 hours. The solution is adjusted to pH 2 with 10% hydrochloric acid and concentrated by evaporation in a vacuum. The residue is dissolved in some water and purified on an ion-exchange column (Reillex®=poly-(4-vinylpyridine)/eluted with water). The main fractions are concentrated by evaporation in a vacuum and the residue is given a final purification by chromatography on RP-18 (LiChroPrep®/mobile solvent: gradient of tetrahydrofuran/methanol/water). After concentration by evaporation of the main fractions, 5.82 g (39% of theory) of an amorphous solid is obtained.

Analysis (relative to the anhydrous substance): C 49.87 H 7.67N 12.92 Cld. C 49.80 H 7.81N 12.88 b) bis-Gadolinium complex of 1,1'-(2,9-dihydroxy-4,7-dioxa-1,10-decyl)-bis[(4,7,10-triscarboxymethyl)-1,4,7,10-tetraazacyclododecane 5 g (5.77 mmol) of the title compound of example 1a is dissolved in 40 ml of deionized water and 2.09 g (5.77 mmol) of gadolinium oxide is added. It is heated for 3 hours to 90° C. The cooled solution is stirred with 2 ml of acid ion exchanger (IR-120) and 2 ml of basic exchanger (IRA-410) each for one hour at room temperature. It is filtered off from the exchanger and the filtrate is boiled up briefly with activated carbon. After filtration and freeze drying, 6.58 g (97% of theory) of an amorphous powder is obtained.

Analysis (relative to the anhydrous substance): C 36.79 H 5.14N 9.53 Gd 26.76 Cld. C 36.71 H 5.21N 9.46 Gd 26.71

Example 2 a) 1,1'-(2,6-Dihydroxy-4-oxa-1,7-heptyl)-bis-[(4,7,10-triscarboxymethyl)-1,4,7,10-tetraazacyclododecane]

Analogously to example 1a, 1,2-6,7-diepoxy-4-oxaheptane was used instead of 1,2-9,10-diepoxy-4,7-dioxadecane.

Yield: 32% of theory of a vitreous solid

Analysis (relative to the anhydrous substance): C 49.63 H 7.59N 13.62 Cld. C 49.58 H 7.65N 13.54 b) bis-Gadolinium complex of 1,1'-(2,6-dihydroxy-4-oxa-1,7-heptyl)-bis-[(4,7,10-triscarboxymethyl)-1,4,7,10-tetraazacyclododecane]

Analogously to example 1b, the title compound of example 2a was used for complexing instead of title compound 1a.

Yield: 96% of theory of a colorless, amorphous powder

Analysis (relative to the anhydrous substance): C 36.10 H 4.99N 9.90 Gd 27.80 Cld. C 36.02 H 5.07N 9.82 Gd 27.73 c) bis-Ytterbium complex of 1,1'-(2,6-dihydroxy-4-oxa-1,7-heptyl)-bis-[(4,7,10-triscarboxymethyl)-1,4,7,10-tetraazacyclododecane]

Analogously to example 1b, ytterbium oxide was used instead of gadolinium oxide.

Yield: 97% of theory of a vitreous solid

Analysis (relative to the anhydrous substance): C 35.11 H 4.85N 9.64 Yb 29.76 Cld. C 35.03 H 4.92N 9.57 Yb 29.68 d) bis-Dysprosium complex of 1,1'-(2,6-dihydroxy-4-oxa-1,7-heptyl)-bis-[(4,7,10-triscarboxymethyl)-1,4,7,10-tetraazacyclododecane]

Analogously to example 1b, dysprosium oxide was used instead of gadolinium oxide.

Yield: 98% of theory of an amorphous powder

Analysis (relative to the anhydrous substance): C 35.76 H 4.94N 9.81 Dy 28.46 Cld. C 35.66 H 5.03N 9.74 Dy 28.40 e) bis-Bismuth complex of 1,1'-(2,6-dihydroxy-4-oxa-1,7-heptyl)-bis-[(4,7,10-triscarboxymethyl)-1,4,7,10-tetraazacyclododecane]

Analogously to example 1b, bismuth oxide was used instead of gadolinium oxide.

Yield: 95% of theory of a colorless, amorphous powder

Analysis (relative to the anhydrous substance): C 33.07 H 4.57N 9.07 Bi 33.85 Cld. C 32.98 H 4.63N 9.00 Bi 33.78

Example 3 a) 1,1'-(2,11-Dihydroxy-4,9-dioxa-dodecyl)-bis-[(4,7,10-triscarboxymethyl)-1,4,7,10-tetraazacyclododecane]

Analogously to example 1a, 1,2-11,12-diepoxy-4,9-dioxa-dodecane was used instead of 1,2-9,10-diepoxy-4,7-dioxadecane.

Yield: 37% of theory of a colorless solid

Analysis (relative to the anhydrous substance): C 51.00 H 7.88N 12.52 Cld. C 49.93 H 7.96N 12.47 b) bis-Gadolinium complex of 1,1'-(2,11-dihydroxy-4,9-dioxa-dodecyl)-bis[(4,7,10-triscarboxymethyl)-1,4,7,10-tetraazacyclododecane]

Analogously to example 1b, the title compound of example 3a was used for complexing instead of title compound 1a.

Yield: 98% of theory of an amorphous powder

Analysis (relative to the anhydrous substance): C 37.92 H 5.36N 9.31 Gd 26.13 Cld. C 37.84 H 5.41N 9.24 Gd 26.08

Example 4 a) 10-(2-Hydroxy-11-benzyloxy-undecyl)-1,4,7-triscarboxymethyl-1,4,7,10-tetraazacyclododecane 28.73 g (103.92 mmol) of 1,2-epoxy-11-benzyloxyundecane and 10 g (28.86 mmol) of 1,4,7-triscarboxymethyl-1,4,7,10-tetraazacyclododecane (=DO3A) are dissolved in a mixture of 50 ml of dioxane/80 ml of water and the pH is brought to pH 10 with 6N potassium hydroxide solution. It is stirred for 24 hours at 70° C. It is evaporated to dryness, the residue is taken up with 200 ml of water/50 ml of methanol and extracted twice with 100 ml of tert-butyl methyl ether. The aqueous solution is adjusted to pH 3 with 5N hydrochloric acid and evaporated to dryness. The residue is boiled out (extracted) with 200 ml of methanol/80 ml of methylene chloride. It is cooled in an ice bath and filtered off from precipitated potassium chloride. The filtrate is concentrated by evaporation in a vacuum, the residue is dissolved in 45 ml of water/20 ml of ethanol and then added to a column of poly-(4-vinylpyridine). The product is eluted with a solution of ethanol/water 1:3. After concentration by evaporation in a vacuum, the residue is chromatographed on a reversed-phase column (RP 18/mobile solvent=gradient of water/tetrahydrofuran). After concentration by evaporation of the main fraction, 12.22 g (68% of theory) of a strongly hygroscopic, vitreous solid is obtained.

Analysis (relative to the anhydrous substance): C 61.71 H 8.74N 9.00 Cld. C 61.82 H 8.91N 8.87 b) Gadolinium complex of 10-(2-hydroxy-11-benzyloxy-undecyl)-1,4,7-tris-carboxymethyl-1,4,7,10-tetraazacyclododecane 10.77 g (17.3 mmol) of the title compound of example 4a is dissolved in 50 ml of deionized water and 3.13 g (8.65 mmol) of gadolinium oxide is added. It is heated for 3 hours to 90° C. The cooled solution is stirred for one hour with 3 ml of acid ion exchanger (AMB 252c) and 3 ml of weak basic exchanger (IRA 67). It is filtered off from the exchanger and the filtrate is freeze-dried.

Yield: 13.17 g (98% of theory) of a colorless, amorphous powder

Analysis (relative to the anhydrous substance): C 49.46 H 6.62N 7.21 Gd 20.24 Cld. C 49.23 H 6.81N 7.15 Gd 20.13 c) Iron complex of 10-(2-hydroxy-11-benzyloxy-undecyl)-1,4,7-tris-carboxymethyl-1,4,7,10-tetraazacyclododecane Analogously to example 4b, iron(III) oxide was used instead of gadolinium oxide.

Yield: 89% of theory of a yellowish powder

Analysis (relative to the anhydrous substance): C 56.88 H 7.61N 8.29 Fe 8.27 Cld. C 56.69 H 7.52N 8.34 Fe 8.18 d) Manganese complex of 10-(2-hydroxy-11-benzyloxy-undecyl)-1,4,7-tris-carboxymethyl-1,4,7,10-tetraazacyclododecane (as sodium salt)

Analogously to example 4b, manganese(2)carbonate was used instead of gadolinium oxide. But it is stirred only with acid exchanger (IR-120). After filtration from the exchanger, the filtrate is brought to pH 7.2 with 1N sodium hydroxide solution and then freeze-dried.

Yield: 93% of theory of a vitreous solid

Analysis (relative to the anhydrous substance): C 55.09 H 7.37N 8.03 Mn 7.87 Na 3.30 Cld. C 55.01 H 7.44N 8.17 Mn 7.71 Na 3.17

Example 5 a) 1,2-Epoxy-11-methoxy-undecane 9.35 g (51.3 mmol) of 1-methoxy-undec(10)ene is dissolved in 100 ml of chloroform. At 0° C., 11.51 g (66.7 mmol) of m-chloroperoxybenzoic acid is added and then allowed to heat to room temperature. It is stirred for 24 hours at room temperature. The precipitated precipitate is filtered off and the filtrate is washed several times with conc. sodium carbonate solution. The organic phase is dried on magnesium sulfate and concentrated by evaporation in a vacuum. The residue is chromatographed on silica gel (mobile solvent: hexane/ethyl acetate 15:1).

Yield: 8.76 g (87% of theory) of a colorless oil.

Analysis (relative to the anhydrous substance): C 73.41 H 12.32 Cld. C 73.28 H 12.41 b) 10-(2-Hydroxy-11-methoxyundecyl)-1,4,7-tris-carboxymethyl-1,4,7,10-tetraazacyclododecane Analogously to example 4a, 1,2-epoxy-11-methoxy-undecane was used instead of the epoxide used in example 4a.

Yield: 75% of theory of a vitreous solid

Analysis (relative to the anhydrous substance): C 57.12 H 9.22N 10.25 Cld. C 57.01 H 9.34N 10.12 c) Gadolinium complex of 10-(2-hydroxy-11-methoxyundecyl)-1,4,7-tris-carboxymethyl-1,4,7,10-tetraazacyclododecane Analogously to example 4b, the title compound of example 5b was used for complexing instead of the title compound of example 4a.

Yield: 97% of theory of a colorless, amorphous powder

Analysis (relative to the anhydrous substance): C 44.55 H 6.76N 8.00 Gd 22.43 Cld. C 44.40 H 6.83N 7.87 Gd 22.31 d) Dysprosium complex of 10-(2-hydroxy-11-methoxyundecyl)-1,4,7-tris-carboxymethyl-1,4,7,10-tetraazacyclododecane Analogously to example 5c, dysprosium oxide was used instead of gadolinium oxide.

Yield: 97% of theory of an amorphous powder

Analysis (relative to the anhydrous substance): C 44.22 H 6.71N 7.93 Dy 23.01 Cld. C 44.10 H 6.83N 7.85 Dy 22.87

Example 6 a) 1-Hydroxy-9-benzyloxy-nonane 16 g (100 mmol) of nonane-1,9-diol was dissolved in 150 ml of dimethylformamide and instilled in a suspension of 2.88 g (1.20 mmol) of sodium hydride in 100 ml of DMF. It is stirred for 2 hours at 50° C. It is cooled in an ice bath to 0° C. and 17.1 g (100 mmol) of benzyl bromide is instilled within 3 hours. Then, it is stirred for 5 hours at 60° C. The solution is cooled to room temperature, 1 l of water is added and it is extracted 3 times with 150 ml of ether. The combined organic phases are dried on magnesium sulfate and concentrated by evaporation in a vacuum. The remaining oil is chromatographed on silica gel (mobile solvent: hexane/acetone=15:1).

Yield: 16.53 g (66% of theory) of a colorless oil

Analysis (relative to the anhydrous substance): C 76.75 H 10.47 Cld. C 76.63 H 10.53 b) 1,2-Epoxy-4-oxa-13-benzyloxy-tridecane 3.56 g (148.5 mmol) of sodium hydride is added to 31 g (123.74 mmol) of 1-hydroxy-9-benzyloxynonane in 400 ml of dimethylformamide and stirred for 1 hour at room temperature (under nitrogen). 34.35 g (371.22 mmol) of epichlorohydrin is added and then heated for 24 hours at 70° C. It is cooled in an ice bath to 0° C. and 800 ml of water is carefully added. Then, it is extracted twice with 350 ml of ether each. The combined ether phases are washed once with 300 ml of water, dried on magnesium sulfate and concentrated by evaporation in a vacuum. The residue is chromatographed on silica gel (mobile solvent: hexane/ethyl acetate= 20:1).

Yield: 26.92 g (71% of theory) of a colorless oil

Analysis (relative to the anhydrous substance): C 74.47 H 9.87 Cld. C 74.29 H 9.98 c) 10-(2-Hydroxy-4-oxa-13-benzyloxy-tridecyl)-1,4,7-triscarboxymethyl-1,4,7,10-tetraazacyclododecane Analogously to example 4a, the title compound of example 6b was used instead of the epoxide used in 4a.

Yield: 68% of theory of a vitreous solid

Analysis (relative to the anhydrous substance): C 60.71 H 8.65N 8.58Cld. C 60.55 H 8.74N 8.47 d) Gadolinium complex of 10-(2-hydroxy-4-oxa-13-benzyloxy-tridecyl)- 1,4,7-triscarboxymethyl-1,4,7,10-tetraazacyclododecane Analogously to example 4b, the title compound of example 6c was used for complexing instead of the title compound of example 4a.

Yield: 95% of theory of a vitreous solid

Analysis (relative to the anhydrous substance): C 49.11 H 6.62N 6.94 Gd 19.48 Cld. C 49.02 H 6.73N 6.85 Gd 19.31

Example 7

10-(2,13-Dihydroxy-4-oxa-tridecyl)-1,4,7-triscarboxymethyl-1,4,7,10-tetraazacyclododecane 15 g (18.59 mmol) of the title compound of example 6d is dissolved in a mixture of 100 ml of water/100 ml of methanol and 3 g of palladium hydroxide (Pearlman catalyst) is added. Then, it is hydrogenated at 40° C. under standard pressure (after 2 hours of complete reaction according to HPLC). It is filtered off from the catalyst and the filtrate is evaporated to dryness in a vacuum.

Yield: 13.06 g (98% of theory) of a colorless, amorphous powder

Analysis (relative to the anhydrous substance): C 43.56 H 6.61N 7.81 Gd 21.93 Cld. C 43.41 H 6.79 N 7.70 Gd 21.80

Example 8 a) 10-(2,6,7-Trihydroxy-4-oxa-heptyl)-1,4,7-triscarboxymethyl-1,4,7,10-tetraazacyclododecane Analogously to example 4a, 2,2-dimethyl-4-(2',13'-epoxy)-propoxy-methyl-1,3-dioxolane was used instead of the epoxide used in example 4a.

Yield: 71% of theory of a colorless solid

Analysis (relative to the anhydrous substance): C 48.57 H 7.74N 11.33 Cld. C 48.46 H 7.81N 11.24 b) Gadolinium complex of 10-(2,6,7-trihydroxy-4-oxa-heptyl)-1,4,7-tris-carboxymethyl-1,4,7,10-tetraazacyclododecane Analogously to example 4b, the title compound of example 8a was used for complexing instead of title compound 4a.

Yield: 98% of theory of an amorphous powder

Analysis (relative to the anhydrous substance): C 37.03 H 5.44N 8.64 Gd 24.24 Cld. C 37.00 H 5.51N 8.57 Gd 24.18 c) Europium complex of 10-(2,6,7-trihydroxy-4-oxa-heptyl)-1,4,7-tris-carboxymethyl-1,4,7,10-tetraazacyclododecane Analogously to example 8b, europium oxide was used instead of gadolinium oxide.

Yield: 96% of theory of an amorphous powder

Analysis (relative to the anhydrous substance): C 37.33 H 5.48N 8.71 Eu 23.62 Cld. C 37.28 H 5.53N 8.66 Eu 23.56 d) Dysprosium complex of 10-(2,6,7-trihydroxy-4-oxa-heptyl)-1,4,7-tris-carboxymethyl-1,4,7,10-tetraazacyclododecane Analogously to example 8b, dysprosium oxide was used instead of gadolinium oxide.

Yield: 96% of theory of an amorphous solid

Analysis (relative to the anhydrous substance): C 36.73 H 5.39N 8.57 Dy 24.85 Cld. C 36.67 H 5.44N 8.51 Dy 24.80 e) Ytterbium complex of 10-(2,6,7-trihydroxy-4-oxa-heptyl)-1,4,7-tris-carboxymethyl-1,4,7,10-tetraazacyclododecane Analogously to example 8b, ytterbium oxide was used instead of gadolinium oxide.

Yield: 97% of theory of an amorphous powder

Analysis (relative to the anhydrous substance): C 36.14 H 5.31N 8.43 Yb 26.04 Cld. C 36.19 H 5.28N 8.38 Yb 25.96

Example 9 a) 2,5,8,13,16,19-hexoxaeicos-10-ene 8.79 g (366.2 mmol) of sodium hydride is added to 40 g (332.9 mmol) of diethylene glycol monomethyl ether in 500 ml of dimethylformamide and stirred for 1 hour at room temperature. Then, 23.74 g (111 mmol) of cis-1,4-dibromo-2-butene is added, and it is heated for 24 hours at 70° C. It is cooled in an ice bath to 0° C. and 1000 ml of water is carefully added. Then, it is extracted twice with 400 ml of ether each. The combined ether phases are washed once with 200 ml of water, dried on magnesium sulfate and concentrated by evaporation in a vacuum. The residue is chromatographed on silica gel (mobile solvent: hexane/ethyl acetate 20:1).

Yield: 15.25 g (47% of theory relative to dibromobutene) of a colorless oil

Analysis (relative to the anhydrous substance): C 57.51 H 9.65 Cld. C 57.58 H 9.57 b) 10,11-Epoxy-2,5,8,13,16,19-hexoxaeicosane 15 g (51.3 mmol) of the title compound of example 9a is dissolved in 100 ml of chloroform. At 0° C., 11.51 g (66.7 mmol) of m-chloroperoxybenzoic acid is added and then it is allowed to heat to room temperature. It is stirred for 24 hours at room temperature. The precipitated precipitate is filtered off and the filtrate is washed several times with conc. sodium carbonate solution. The organic phase is dried on magnesium sulfate and concentrated by evaporation in a vacuum. The residue is chromatographed on silica gel (mobile solvent: hexane/ethyl acetate 15:1).

Yield: 13.76 (87% of theory) of a colorless oil

Analysis (relative to the anhydrous substance): C 54.53 H 9.15 Cld. C 54.47 H 9.06 c) 10-(1-(2,5,8-Trioxanonyl)-2-hydroxy-4,7,10-trioxa-undecanyl)]-1,4,7-triscarboxymethyl-1,4,7,10-tetraazacyclododecane Analogously to example 4a, 10,11-epoxy-2,5,8,13,16,19-hexoxaeicosane was used instead of the epoxide used in example 4a.

Yield: 34% of theory of a vitreous solid

Analysis (relative to the anhydrous substance): C 51.36 H 8.31N 8.56 Cld. C 51.27 H 8.40N 8.51 d) Gadolinium complex of 10-[1-(2,5,8-trioxanonyl)-2-hydroxy-4,7,10-trioxa-undecanyl)]-1,4,7-triscarboxymethyl-1,4,7,10-tetraazacyclododecane Analogously to example 4b, the title compound of example 9c was used for complexing instead of the title compound of example 4a.

Yield: 97% of theory of a colorless, amorphous powder

Analysis (relative to the anhydrous substance): C 41.57 H 6.35N 6.93 Gd 19.44 Cld. C 41.48 H 6.41N 6.91 Gd 19.37

Example 10 a) 9,14-Dioxa-docos(11)ene

Analogously to example 9a, n-octanol was used instead of diethylene glycol monomethyl ether.

Yield: 59% of theory of a colorless oil

Analysis (relative to the anhydrous substance): C 76.86 H 12.90 Cld. C 76.78 H 12.84 b) 11,12-Epoxy-9,14-dioxa-docosane

Analogously to example 9b, the title compound of example 10a was used instead of title compound 9a.

Yield: 83% of theory of a colorless oil C 73.12 H 12.2 7 Cld. C 73.04 H 12.34 c) 10-l-(2-Oxadecyl)-2-hydroxy-4-oxa-dodecyl]-1,4,7-triscarboxymethyl-1,4,7,10-tetraazacyclododecane Analogously to example 4a, 11,12-epoxy-9,14-dioxadocosane was used instead of the epoxide used in example 4a.

Yield: 37% of theory of a colorless solid

Analysis (relative to the anhydrous substance): C 60.51 H 9.86N 8.30 Cld. C 60.46 H 9.94N 8.25 d) Gadolinium complex of 10-[1-(2-oxadecyl)-2-hydroxy-4-oxa-dodecyl]-1,4,7-tris-carboxymethyl-1,4,7,10-tetraazacyclododecane Analogously to example 4b, the title compound of example 10c was used for complexing instead of title compound 4a.

Yield: 96% of theory of a colorless powder

Analysis (relative to the anhydrous substance): C 49.25 H 7.66N 6.76 Gd 18.97 Cld. C 49.17 H 7.80N 6.68 Gd 18.91

Example 11 a) 10-(2-Hydroxy-5-phenyl-4-oxa-pentyl)-1,4,7-tris(carboxymethyl)-1,4,7,10-tetraazacyclododecane 10.2 g (29.45 mmol) of 1,4,7-triscarboxymethyl-1,4,7,10-tetraazacyclododecane (=DO3A) and 8.7 g (53.0 mmol) of benzyl-2,3-epoxypropylether are dissolved in a mixture of 50 ml of dioxane and 80 ml of water, and the pH is brought to pH 10 with 6N potassium hydroxide solution. It is stirred for 24 hours at 40° C. It is evaporated to dryness, the residue is taken up with 200 ml of water/50 ml of methanol and extracted twice with 100 ml of tert-butyl methyl ether. The aqueous solution is adjusted to pH 3 with 5N hydrochloric acid and evaporated to dryness. The residue is concentrated by evaporation in a vacuum and boiled out (extracted) with 200 ml of methanol/50 ml of methylene chloride. It is cooled in an ice bath and filtered off from the precipitated potassium chloride. The filtrate is concentrated by evaporation in a vacuum, the residue is dissolved in 45 ml of water and then added on a column of poly-(4-vinylpyridine). The product is eluted with a solution of ethanol/water=1:5. After concentration by evaporation in a vacuum, 11.58 g (77% of theory) of the title compound is obtained as strongly hygroscopic, vitreous solid.

Analysis (relative to the anhydrous substance): C 56.46 H 7.50N 10.97Cld. C 56.41 H 7.58N 10.81 b) Gadolinium complex of 10-(2-hydroxy-5-phenyl-4-oxa-pentyl)-1,4,7-tris(carboxymethyl)-1,4,7,10-tetraazacyclododecane 10.0 g (19.59 mmol) of the title compound of example 11a is dissolved in 70 ml of deionized water and 3.55 g (9.79 mmol) of gadolinium oxide is added. It is heated for 3 hours to 90° C. The cooled solution is stirred with 3 ml of acid ion exchanger (IR 120) and 3 ml of basic exchanger (IRA 410) each for one hour at room temperature. After filtration from the exchanger, the filtrate is freeze-dried.

Yield: 12.5 g (96% of theory) of an amorphous powder

Analysis (relative to the anhydrous substance): C 43.36 H 5.31N 8.43 Gd 23.65 Cld. C 43.31 H 5.37N 8.41 Gd 23.58 c) 151Europium complex of 10-(2-hydroxy-5-phenyl-4-oxa-pentyl)-1,4,7-tris(carboxymethyl)-1,4,7,10-tetraazacyclododecane Analogously to example 11b, [151]europium oxide was used instead of gadolinium oxide.

Yield: 95% of theory of an amorphous powder

Analysis (relative to the anhydrous substance): C 42.79 H 5.15N 8.68 Eu 23.54 Cld. C 42.72 H 5.10N 8.73 Eu 23.48 d) Ytterbium complex of 10-(2-hydroxy-5-phenyl-4-oxa-pentyl)-1,4,7-tris(carboxymethyl)-1,4,7,10-tetraazacyclododecane Analogously to example 11b, ytterbium oxide was used instead of gadolinium oxide.

Yield: 98% of theory of an amorphous powder

Analysis (relative to the anhydrous substance): C 41.44 H 4.99N 8.41 Yb 25.96 Cld. C 41.37 H 5.05N 8.37 Yb 25.91

Example 12 a) 10-[3-(4-Nitrophenoxy)-2-hydroxypropyl]-1,4,7-tris(carboxymethyl)-1,4,7,10-tetraazacyclododecane 12.68 g (64.95 mmol) of 4-nitrophenyl-2,3-epoxypropylether and 12.5 g (36.08 mmol) of 1,4,7-triscarboxymethyl-1,4,7,10-tetraazacyclododecane (=DO3A) are dissolved in a mixture of 70 ml of dioxane and 80 ml water, and the pH is brought to pH 10 with 6N sodium hydroxide solution. It is stirred for 24 hours at 40° C. It is evaporated to dryness, the residue is taken up with 200 ml of water/50 ml of methanol and extracted twice with 100 ml of ethyl acetate. The aqueous solution is adjusted to pH 3 with 5N hydrochloric acid and evaporated to dryness. The residue is concentrated by evaporation in a vacuum and boiled out (extracted) with 200 ml of methanol/50 ml of methylene chloride. It is cooled in an ice bath and filtered off from precipitated potassium chloride. The filtrate is concentrated by evaporation in a vacuum, the residue is dissolved in 50 ml of water/30 ml of ethanol and then added on a column of poly-(4-vinylpyridine). The product is eluted with ethanol/water =1:4. After concentration by evaporation in a vacuum, 14.43 g (74% of theory) of the title compound is obtained as strongly hygroscopic, vitreous solid.

Analysis (relative to the anhydrous substance): C 51.11 H 6.34N 12.96Cld. C 51.07 H 6.41N 12.90 b) Gadolinium complex of 10-[3-(4-nitrophenoxy)-2-hydroxypropyl]-1,4,7-tris(carboxymethyl)-1,4,7,10-tetraazacyclododecane 14.1 g (26.08 mmol) of the title compound of example 12a is dissolved in 100 ml of deionized water and 4.73 g (13.04 mmol) of gadolinium oxide is added. It is stirred for 3 hours at 90° C. The cooled solution is stirred with 3 ml of ion exchanger (IR 120) and 3 ml of basic exchanger (IRA 410) each for one hour. It is filtered from the exchanger and evaporated to dryness in a vacuum.

Yield: 17.4 g (96% of theory) of a vitreous solid

Analysis (relative to the anhydrous substance): C 39.76 H 4.50N 10.08 Gd 22.63 Cld. C 39.70 H 4.53N 10.12 Gd 22.57 c) Gadolinium complex of 10-[3-(4-aminophenoxy)-2-hydroxypropyl]-1,4,7-tris(carboxymethyl)-1,4,7,10-tetraazacyclododecane 15.0 g (21.59 mmol) of the title compound of example 12b is dissolved in 250 ml of deionized water and 3 g of palladium catalyst (10% Pd on activated carbon) is added. It is hydrogenated for 2 hours at 40° C. (according to HPLC, a complete conversion takes place). It is filtered off from the catalyst and evaporated to dryness in a vacuum.

Yield: 14.07 g (98% of theory) of a vitreous solid

Analysis (relative to the anhydrous substance): C 41.55 H 5.00N 10.53 Gd 23.65 Cld. C 41.50 H 5.09N 10.49 Gd 23.58 d) Gadolinium complex of 10-[3-(4-isothiocyanatophenoxy)-2-hydroxypropyl]-1,4,7-tris(carboxymethyl)-1,4,7,10-tetraazacyclododecane 10.0 g (15.04 mmol) of the title compound of example 12c and 30 ml of polyvinylpyridine (Reillex) are dissolved in 200 ml of deionized water and 5.19 g (45.13 mmol) of thiophosgene (in 150 ml of chloroform) is added. It is stirred for 10 minutes at 40° C., then for 1 hour at room temperature. The two-phase solution is filtered off from the Reillex and then the organic phase is separated. The aqueous phase is extracted twice with 100 ml of chloroform and then freeze-dried.

Yield: 10.31 g (97% of theory) of a white, amorphous powder

Analysis (relative to the anhydrous substance): C 40.78 H 4.42N 9.91 Gd 22.25 S 4.54 Cld. C 40.67 H 4.51N 9.85 Gd 22.19 S 4.48

Example 13 a) 10-(2-Hydroxy-3-phenoxy-propyl)-1,,7-tris(carboxymethyl)-1,4,7,10-tetraazacyclododecane 7.8 g (51.96 mmol) of phenyl-2,3-epoxypropylether and 10 g (28.87 mmol) of 1,4,7-triscarboxymethyl-1,4,7,10-tetraazacyclododecane (=DO3A) are dissolved in a mixture of 50 ml of dioxane and 80 ml of water and the pH is brought to pH 10 with 6N potassium hydroxide solution. It is stirred for 24 hours at 40° C. It is evaporated to dryness, the residue is taken up with 200 ml of water/50 ml of methanol and extracted twice with 100 ml of tert-butyl methyl ether. The aqueous solution is adjusted to pH 3 with 5N hydrochloric acid and evaporated to dryness. The residue is concentrated by evaporation in a vacuum and boiled out (extracted) with 200 ml of methanol/80 ml of methylene chloride. It is cooled in an ice bath and filtered off from precipitated potassium chloride. The filtrate is concentrated by evaporation in a vacuum, the residue is dissolved in 50 ml of water/20 ml of ethanol and then added on a column of poly-(4-vinylpyridine). The product is eluted with a solution of ethanol/water=1:3. After concentration by evaporation in a vacuum, 8.17 g (57% of theory) of the title compound is obtained as a strongly hygroscopic, vitreous solid.

Analysis (relative to the anhydrous substance): C 55.63 H 7.31N 11.28Cld. C 55.59 H 7.38N 11.24 b) Gadolinium complex of 10-(2-hydroxy-3-phenoxy-propyl)-1,4,7-tris(carboxymethyl)-1,4,7,10-tetraazacyclododecane 7.8 g (15.71 mmol) of the title compound of example 13a is dissolved in 50 ml of deionized water and 2.85 g (7.85 mmol) of gadolinium oxide is added. It is heated for 3 hours to 90° C. The cooled solution is stirred with 3 ml of acid ion exchanger (IR 120) and 3 ml of basic exchanger (IRA 410) each for one hour at room temperature. After filtration from the exchanger, the filtrate is freeze-dried.

Yield: 9.71 g (95% of theory) of a colorless, amorphous powder

Analysis (relative to the anhydrous substance): C 42.45 H 5.11N 8.61 Gd 24.16 Cld. C 42.38 H 5.19N 8.56 Gd 24.09

Example 14 a) 10-[2-Hydroxy-3-(4-methoxyphenoxy)-propyl]-1,4,7-tris(carboxymethyl)-1,4,7,10-tetraazacyclododecane 9.36 g (51.96 mmol) of 4-methoxyphenyl-2,3-epoxypropylether and 10 g (51.96 mmol) of 1,4,7-triscarboxymethyl-1,4,7,10-tetraazacyclododecane (=DO3A) are dissolved in a mixture of 50 ml of dioxane and 80 ml of water and the pH is brought to pH 10 with 6N potassium hydroxide solution. It is stirred for 24 hours at 40° C. It is evaporated to dryness, the residue is taken up with 200 ml of water/50 ml of methanol and extracted twice with 100 ml of tert-butyl methyl ether. The aqueous solution is adjusted to pH 13 with 5N hydrochloric acid and evaporated to dryness. The residue is concentrated by evaporation in a vacuum and boiled out (extracted) with 200 ml of methanol/80 ml of methylene chloride. It is cooled in an ice bath and filtered off from precipitated potassium chloride. The filtrate is concentrated by evaporation in a vacuum, the residue is dissolved in 45 ml of water/20 ml of ethanol and then added to a column of poly-(4-vinylpyridine). The product is eluted with a solution of ethanol/water=1:3. After concentration by evaporation in a vacuum, 9.27 g (61% of theory) of the title compound is obtained as strongly hygroscopic, vitreous solid.

Analysis (relative to the anhydrous substance): C 54.74 H 7.27N 10.46 Cld. C 54.71 H 7.30N 10.57 b) Gadolinium complex of 10-[2-hydroxy-3-(4-methoxyphenoxy)-propyl]-1,4,7-tris(carboxymethyl)-1,4,7,10-tetraazacyclododecane 8.8 g (16.71 mmol) of the title compound of example 14a is dissolved in 60 ml of deionized water and 3.03 g (8.36 mmol) of gadolinium oxide is added. It is heated for 3 hours to 90° C. The cooled solution is stirred with 3 ml of acid ion exchanger (IR 120) and 3 ml of basic exchanger (IRA 410) each for one hour at room temperature. After filtration from the exchanger, the filtrate is freeze-dried.

Yield: 11.04 g (97% of theory) of a colorless, amorphous powder

Analysis (relative to the anhydrous substance): C 42.34 H 5.18N 8.23 Gd 23.10 Cld. C 42.28 H 5.23N 8.17 Gd 23.03

Example 15 a) 6,7-Epoxy-4-oxa-1-[4-(methoxy)-phenyl]-heptane

Analogously to example 6b, 3-(4-methoxyphenyl)-propan-1-ol was used instead of the title compound of example 6a.

Yield: 38% of theory of a colorless, viscous oil. C 70.24 H 8.16 Cld. C 70.31 H 8.20 b) 10-[2-Hydroxy-4-oxa-7-(4-methoxyphenyl)-heptyl]-1,4,7-tris(carboxymethyl)-1,4,7,10-tetraazacyclododecane 10.93 g (51.96 mmol) of 6,7-epoxy-4-oxa-1-[4-(methoxy)phenyl]heptane and 10 g (28.87 mmol) of 1,4,7-triscarboxymethyl-1,4,7,10-tetraazacyclododecane (=DO3A) are dissolved in a mixture of 60 ml of dioxane and 90 ml of water, and the pH is brought to pH 10 with 6N potassium hydroxide solution. It is stirred for 24 hours at 40° C. It is evaporated to dryness, the residue is taken up with 200 ml of water/50 ml of methanol and extracted twice with 100 ml of tert-butyl methyl ether. The aqueous solution is adjusted to pH 3 with 5N hydrochloric acid and evaporated to dryness. The residue is concentrated by evaporation in a vacuum and boiled out (extracted) with 200 ml of methanol/80 ml of methylene chloride. It is cooled in an ice bath and filtered off from precipitated potassium chloride. The filtrate is concentrated by evaporation in a vacuum, the residue is dissolved in 45 ml of water/20 ml of ethanol and then added on a column of poly-(4-vinylpyridine). The product is eluted with a mixture of ethanol/water=1:3. After concentration by evaporation in a vacuum, 9.69 g (59% of theory) of the title compound is obtained as strongly hygroscopic, vitreous solid.

Analysis (relative to the anhydrous substance): C 57.03 H 7.80N 9.85Cld. C 57.10 H 7.85N 9.79 c) Gadolinium complex of 10-[2-hydroxy-4-oxa-7-(4-methoxyphenyl)-heptyl]-1,4,7-tris(carboxymethyl)-1,4,7,10-tetraazacyclododecane 9.2 g (16.18 mmol) of the title compound of example 15b is dissolved in 80 ml of deionized water and 2.93 g (8.09 mmol) of gadolinium oxide is added. It is heated for 3 hours to 90° C. The cooled solution is stirred with 3 ml of acid ion exchanger (IR 120) and 3 ml of basic exchanger (IRA 410) each for one hour at room temperature. After filtration from the exchanger, the filtrate is freeze-dried.

Yield: 11.34 g (97% of theory) of a colorless, amorphous powder

Analysis (relative to the anhydrous substance): C 44.86 H 5.72N 7.75 Gd 21.75 Cld. C 44.79 H 5.81N 7.69 Gd 21.68

Example 16 a) 10-[3-(4-Chlorophenoxy)-2-hydroxypropyl]-1,4,7-tris(carboxymethyl)-1,4,7,10-tetraazacyclododecane 9.59 g (21.96 mmol) of 4-chlorophenyl-2,3-epoxypropylether and 10 g (28.87 mmol) of 1,4,7-triscarboxymethyl-1,4,7,10-tetraazacyclododecane (=DO3A) are dissolved in a mixture of 50 ml of dioxane and 80 ml of water and the pH is brought to pH 10 with 6N potassium hydroxide solution. It is stirred for 24 hours at 40° C. It is evaporated to dryness, the residue is taken up with 200 ml of water/50 ml of methanol and extracted twice with 100 ml of tert-butyl methyl ether. The aqueous solution is adjusted to pH 3 with 5N hydrochloric acid and evaporated to dryness. The residue is concentrated by evaporation in a vacuum and boiled out (extracted) with 200 ml of methanol/80 ml of methylene chloride. It is cooled in an ice bath and filtered off from precipitated potassium chloride. The filtrate is concentrated by evaporation in a vacuum, the residue is dissolved in 45 ml of water/20 ml of ethanol and then added on a column of poly-(4-vinylpyridine). The product is eluted with a solution of ethanol/water=1:3. After concentration by evaporation in a vacuum, 8.28 g (54% of theory) of the title compound is obtained as strongly hygroscopic, vitreous solid.

Analysis (relative to the anhydrous substance): C 52.02 H 6.64N 10.55 Cl 6.68 Cld. C 52.05 H 6.71N 10.49 Cl 6.60 b) Gadolinium complex of 10-[3-(4-chlorophenoxy)-2-hydroxypropyl]-1,4,7-tris(carboxymethyl)-1,4,7,10-tetraazacyclododecane 7.9 g (14.88 mmol) of the title compound of example 16a is dissolved in 60 ml of deionized water and 2.70 g (7.44 mmol) of gadolinium oxide is added. It is heated for 3 hours to 90° C. The cooled solution is stirred with 3 ml of acid ion exchanger (IR 120) and 3 ml of basic exchanger (IRA 410) each for one hour at room temperature. After filtration from the exchanger, the filtrate is freeze-dried.

Yield: 9.79 g (96% of theory) of a colorless, amorphous powder

Analysis (relative to the anhydrous substance): C 40.32 H 4.71N 8.18 Gd 22.95 Cl 5.17 Cld. C 40.27 H 4.80N 8.09 Gd 22.91 Cl 5.10

Example 17 a) 2,3-Epoxy-l-[4-(5-hydroxypentyl)-phenoxy]-propane

Analogously to example 6b, 5-(4-hydroxyphenyl)-pentan-1-ol was used instead of the title compound of example 6a.

Yield: 51% of theory of a colorless oil

Analysis (relative to the anhydrous substance): C 71.16 H 8.53 Cld. C 71.08 H 8.62 b) 10-[2-Hydroxy-3-(4-(5-hydroxypentyl)-phenoxy)-propyl]-1,4,7-tris(carboxymethyl)-1,4,7,10-tetraazacyclododecane 12.3 g (51.97 mmol) of 2,3-epoxy-1-[4-(5-hydroxypentyl)-phenoxy]-propane and 10 g (28.87 mmol) of 1,4,7-triscarboxymethyl-1,4,7,10-tetraazacyclododecane (=DO3A) are dissolved in a mixture of 50 ml of dioxane and 80 ml of water, and the pH is brought to pH 10 with 6N potassium hydroxide solution. It is stirred for 24 hours at 40° C. It is evaporated to dryness, the residue is taken up with 200 ml of water/50 ml of methanol and extracted twice with 100 ml of tert-butyl methyl ether. The aqueous solution is adjusted to pH 3 with 5N hydrochloric acid and evaporated to dryness. The residue is concentrated by evaporation in a vacuum and boiled out (extracted) with 200 ml of methanol/50 ml of methylene chloride. It is cooled in an ice bath and filtered off from precipitated potassium chloride. The filtrate is concentrated by evaporation in a vacuum, the residue is dissolved in 50 ml of water/20 ml of ethanol and then added to a column of poly-(4-vinylpyridine). The product is eluted with a solution of ethanol/water. After concentration by evaporation in a vacuum, 8.92 g (53% of theory) of the title compound is obtained as strongly hygroscopic, vitreous solid.

Analysis (relative to the anhydrous substance): C 57.72 H 7.72N 9.62Cld. C 57.68 H 7.79N 9.54 c) Gadolinium complex of 10-[2-hydroxy-3-(4-(5-hydroxypentyl)-phenoxy)-propyl]-1,4,7-tris(carboxymethyl)-1,4,7,10-tetraazacyclododecane 8.7 g (14.93 mmol) of the title compound of example 17b is dissolved in 70 ml of deionized water and 2.71 g (7.47 mmol) of gadolinium oxide is added. It is heated for 3 hours to 90° C. The cooled solution is stirred with 3 ml of acid ion exchanger (IR 120) and 3 ml of basic exchanger (IRA 410) each for one hour at room temperature. After filtration from the exchanger, the filtrate is freeze-dried.

Yield: 10.67 g (97% of theory) of a colorless, amorphous powder

Analysis (relative to the anhydrous substance): C 45.64 H 5.88N 7.60 Gd 21.34 Cld. C 45.60 H 5.93N 7.54 Gd 21.28

Example 18 a) 10-[3-(2,6-Dimethylphenoxy)-2-hydroxypropyl]-1,4,7-tris(carboxymethyl)-1,4,7,10-tetraazacyclododecane 9.59 g (51.96 mmol) of 2,6-dimethylphenyl-2,3-epoxypropylether and 10 g (28.87 mmol) of 1,4,7-tris-carboxymethyl-1,4,7,10-tetraazacyclododecane (=DO3A) are dissolved in a mixture of 50 ml of dioxane and 80 ml of water and the pH is brought to pH 10 with 6N potassium hydroxide solution. It is stirred for 24 hours at 40° C. It is evaporated to dryness, the residue is taken up with 200 ml of water/50 ml of methanol and extracted twice with 100 ml of tert-butyl methyl ether. The aqueous solution is adjusted to pH 3 with 5N hydrochloric acid and evaporated to dryness. The residue is boiled out (extracted) with 200 ml of methanol/80 ml of methylene chloride. It is cooled in an ice bath and filtered off from precipitated potassium chloride. The filtrate is concentrated by evaporation in a vacuum, the residue is dissolved in 50 ml of water and 30 ml of ethanol and then added to a column of poly-(4-vinylpyridine). The product is eluted with a solution of ethanol/water=1:3. After concentration by evaporation in a vacuum, 9.24 g (61% of theory) of the title compound is obtained as strongly hygroscopic, vitreous solid.

Analysis (relative to the anhydrous substance): C 57.24 H 7.68N 10.68 Cld. C 57.18 H 7.74 N 10.64 b) Gadolinium complex of 10-[3-(2,6-dimethylphenoxy)-2-hydroxypropyl]-1,4,7-tris(carboxymethyl)-1,4,7,10-tetraazacyclododecane 9.0 g (17.16 mmol) of the title compound of example 18a is dissolved in 70 ml of deionized water and 3.11 g (8.58 mmol) of gadolinium oxide is added. It is heated for 3 hours to 90° C. The cooled solution is stirred with 3 ml of acid ion exchanger (IR 120) and 3 ml of basic exchanger (IRA 410) each for one hour at room temperature. After filtration from the exchanger, the filtrate is freeze-dried.

Yield: 11.30 g (97% of theory) of a colorless, amorphous powder

Analysis (relative to the anhydrous substance): C 44.23 H 5.49N 8.25 Gd 23.16 Cld. C 44.18 H 5.54N 8.20 Gd 23.08

Example 19 a) 2,3-Epoxy-1-[4-(ethoxycarbonylmethyl)-phenoxy]-propane

Analogously to example 6b, 4-hydroxyphenylethyl-acetate was used instead of the title compound of example 6a.

Yield: 61% of theory of a colorless, viscous oil.

Analysis (relative to the anhydrous substance): C 66.09 H 6.83 Cld. C 66.14 H 6.74 b) 10-[2-Hydroxy-3-(4-(carboxymethyl)-phenoxy)-propyl]-1,4,7-tris(carboxymethyl)-1,4,7,10-tetraazacyclododecane 10 g (28.87 mmol) of 1,4,7-triscarboxymethyl-1,4,7,10-tetraazacyclododecane (=DO3A) and 12.99 g (51.96 mmol) of 2,3-epoxy-1-[4-(2-ethoxycarbonylmethyl)-phenoxy]-propane are added in 80 ml of dioxane/60 ml of water and adjusted to pH 13 with 6N potassium hydroxide solution. It is stirred for 12 hours at room temperature. Then, it is refluxed for 2 hours. It is adjusted with 5N hydrochloric acid to pH 7 and evaporated to dryness in a vacuum. The residue is absorptively precipitated in 200 ml of ethanol/50 ml of chloroform at 60° C. The precipitated potassium chloride is filtered off and the filtrate is concentrated by evaporation in a vacuum. The residue is purified on a reversed-phase column (RP-18, washing with water, then elution with tetrahydrofuran/water=2:1). The main fractions are concentrated by evaporation in a vacuum.

Yield: 8.32 g (52% of theory) of a vitreous solid

Analysis (relative to the anhydrous substance): C 54.14 H 6.91N 10.10 Cld. C 54.06 H 6.98N 10.06 c) Gadolinium complex of 10-[2-hydroxy-3-(4-(carboxymethyl)-phenoxy)-propyl]- 1,4,7-tris(carboxymethyl)-1,4,7,10-tetraazacyclododecane (as sodium salt)

8.1 g (14.61 mmol) of the title compound of example 19b is dissolved in 60 ml of deionized water and 2.65 g (7.30 mmol) of gadolinium oxide is added. It is heated for 3 hours to 90° C. The cooled solution is stirred at room temperature for one hour with 7 ml of weak acid ion exchanger (AMB 252c). It is filtered off from the exchanger. The filtrate is adjusted to pH 7.2 with 2N sodium hydroxide solution and freeze-dried.

Yield: 10.14 g (95.5 of theory) of a colorless, amorphous powder

Analysis (relative to the anhydrous substance): C 41.09 H 4.69N 7.67 Gd 21.52 Na 3.15 Cld. C 41.04 H 4.78 N 7.61 Gd 21.47 Na 3.19

Example 20 a) 2,3-Epoxy-1-[4-(ethoxycarbonyl)-cyclohexyloxy]-propane

Analogously to example 6b, 4-hydroxy-cyclohexane-carboxylic acid ethyl ester was used instead of the title compound of example 6a.

Yield: 33% of theory of a colorless oil

Analysis (relative to the anhydrous substance): C 63.14 H 8.33 Cld. C 63.07 H 8.91 b) 10-[2-Hydroxy-3-(4-(carboxy)-cyclohexyloxy)-propyl]-1,4,7-tris(carboxymethyl)-1,4,7,10-tetraazacyclododecane 10 g (28.87 mmol) of 1,4,7-triscarboxymethyl-1,4,7,10-tetraazacyclododecane (=DO3A) and 12.99 g (51.96 mmol) of 2,3-epoxy-1-[4-(ethoxycarbonyl)-cyclohexyloxy]-propane are added in 80 ml of dioxane/60 ml of water and adjusted to pH 13 with 6N potassium hydroxide solution. It is stirred for 12 hours at room temperature. Then, it is refluxed for 2 hours. It is adjusted to pH 7 with 5N hydrochloric acid and evaporated to dryness in a vacuum. The residue is absorptively precipitated in 200 ml of ethanol/50 ml of chloroform at 60° C. The precipitated potassium chloride is filtered off and the filtrate is concentrated by evaporation in a vacuum. The residue is purified on a reversed-phase column (RP-18, washing with water, then elution with tetrahydrofuran/water=2:1). The main fractions are concentrated by evaporation in a vacuum.

Yield: 8.2 g (52% of theory) of a vitreous solid

Analysis (relative to the anhydrous substance): C 52.74 H 7.74N 10.25 Cld. C 52.68 H 7.81N 10.19 c) Gadolinium complex of 10-[2-hydroxy-3-(4-(carboxy)-cyclohexyloxy)-propyl]-1,4,7-tris(carboxymethyl)-1,4,7,10-tetraazacyclododecane (as sodium salt)

8.0 g (14.64 mmol) of the title compound of example 20b is dissolved in 70 ml of deionized water and 2.66 g (7.32 mmol) of gadolinium oxide is added. It is heated for 3 hours to 90° C. The cooled solution is stirred for one hour with 10 ml of a weak acid ion exchanger (AMB 252c) at room temperature. It is filtered off from the exchanger. The filtrate is adjusted to pH 7.2 with 2N sodium hydroxide solution and freeze-dried.

Yield: 9.84 g (93% of theory) of a colorless, amorphous powder

Analysis (relative to the anhydrous substance): C 39.88 H 5.30N 7.75 Gd 21.75 Na 3.13 Cld. C 39.81 H 5.37N 7.69 Gd 21.70 Na 3.25

Example 21 a) 2,3-Epoxy-1-[4-(2-ethoxycarbonylethyl)-phenoxy]-propane

Analogously to example 6b, 2-(4-hydroxyphenyl)-propanoic acid ethyl ester was used instead of the title compound of example 6a.

Yield: 67% of theory of a colorless oil

Analysis (relative to the anhydrous substance): C 67.18 H 7.25 Cld. C 67.09 H 7.32 b) 10-[2-Hydroxy-3-(4-(2-carboxyethyl)-phenoxy)-propyl]-1,4,7-tris(carboxymethyl)-1,4,7,10-tetraazacyclododecane 10 g (28.87 mmol) of 1,4,7-triscarboxymethyl-1,4,7,10-tetraazacyclododecane (=DO3A) and 12.99 g (51.96 mmol) of 2,3-epoxy-1-[4-(2-ethoxycarbonylethyl)-phenoxy]-propane are added in 80 ml of dioxane/60 ml of water and adjusted to pH 14 with 6N potassium hydroxide solution. It is stirred for 12 hours at room temperature. Then, it is refluxed for 2 hours. It is adjusted to pH 7 with 5N hydrochloric acid and evaporated to dryness in a vacuum. The residue is absorptively precipitated in 200 ml of ethanol/50 ml of chloroform at 60° C. The precipitated potassium chloride is filtered off and the filtrate is concentrated by evaporation in a vacuum. The residue is purified on a reversed-phase column (RP-18, washing with water, then elution with tetrahydrofuran/water=2:1). The main fractions are concentrated by evaporation in a vacuum.

Yield: 7.88 g (48% of theory) of a vitreous solid

Analysis (relative to the anhydrous substance): C 54.92 H 7.09N 9.85 Cld. C 54.87 H 7.15N 9.79 c) Gadolinium complex of 10-[2-hydroxy-3-(4-(2-carboxyethyl)-phenoxy)-propyl]-1,4,7-tris(carboxymethyl)-1,4,7,10-tetraazacyclododecane (as sodium salt)

7.5 g (13.19 mmol) of the title compound of example 21b is dissolved in 50 ml of deionized water and 2.39 g (6.59 mmol) of gadolinium oxide is added. It is heated for 3 hours to 90° C. The cooled solution is stirred for one hour with 7 ml of weak acid ion exchanger (AMB 252c) at room temperature. It is filtered off from the exchanger. The filtrate is adjusted to pH 7.2 with 2N sodium hydroxide solution and freeze-dried.

Yield: 9.23 g (94% of theory) of a colorless, amorphous powder

Analysis (relative to the anhydrous substance): C 41.93 H 4.87N 7.52 Gd 21.11 Na 3.09 Cld. C 41.87 H 4.93N 7.47 Gd 21.06 Na 3.14

Example 22 a) 2,3-Epoxy-1-[4-(2-ethoxycarbonyl-1-oxa-ethyl)-phenoxy]-propane

Analogously to example 6b, 4-hydroxyphenoxyethyl-acetate was used instead of the title compound of example 6a.

Yield: 57% of theory of a colorless oil

Analysis (relative to the anhydrous substance): C 61.89 H 6.39 Cld. C 61.78 H 6.43 b) 10-[2-Hydroxy-3-(4-(2-carboxy-1-oxa-ethyl)-phenoxy)-propyl]-1,4,7-tris(carboxymethyl)-1,4,7,10-tetraazacyclododecane 10 g (28.87 mmol) of 1,4,7-triscarboxymethyl-1,4,7,10-tetraazacyclododecane (-DO3A) and 12.99 g (51.96 mmol) of 2,3-epoxy-1-[4-(2-ethoxycarbonylethyl)-phenoxy]-propane are added in 80 ml of dioxane/60 ml of water and adjusted to pH 13 with 6N potassium hydroxide solution. It is stirred for 12 hours at room temperature. Then, it is refluxed for 2 hours. It is adjusted to pH 7 with 5N hydrochloric acid and evaporated to dryness in a vacuum. The residue is absorptively precipitated in 200 ml of ethanol/50 ml of chloroform at 60° C. The precipitated potassium chloride is filtered off and the filtrate is concentrated by evaporation in a vacuum. The residue is purified on a reversed-phase column (RP-18, washing with water, then elution with tetrahydrofuran/water=2:1). The main fractions are concentrated by evaporation in a vacuum.

Yield: 8.40 g (51% of theory) of a vitreous solid

Analysis (relative to the anhydrous substance): C 52.62 H 6.71N 9.82 Cld. C 52.58 H 6.78N 9.77 b) Gadolinium complex of 10-[2-hydroxy-3-(4-(2-carboxy-1-oxa-ethyl)-phenoxy)-propyl]-1,4,7-tris(carboxymethyl)-1,4,7,10-tetraazacyclododecane (as sodium salt)

8.1 g (14.2 mmol) of the title compound of example 22b is dissolved in 70 ml of deionized water and 2.57 g (7.1 mmol) of gadolinium oxide is added. It is heated for 3 hours to 90° C. The cooled solution is stirred for one hour with 8 ml of weak acid ion exchanger (AMB 252c) at room temperature. It is filtered off from the exchanger. The filtrate is adjusted to pH 7.2 with 2N sodium hydroxide solution and freeze-dried.

Yield: 9.86 g (93% of theory) of an amorphous powder

Analysis (relative to the anhydrous substance): C 40.21 H 4.59N 7.50 Gd 21.06 Na 3.08 Cld. C 40.16 H 4.65N 7.47 Gd 21.00 Na 3.15

Example 23 a) 2,3-Epoxy-1-[4-(ethoxycarbonyl)-phenoxy]-propane

Analogously to example 6b, 4-hydroxy-phenylcarboxylic acid ethyl ester was used instead of the title compound of example 6a.

Yield: 73% of theory of a colorless oil

Analysis (relative to the anhydrous substance): C 64.85 H 6.35 Cld. C 64.78 H 6.43 b) 10-[2-Hydroxy-3-(4-(carboxy)-phenoxy)-propyl]-1,4,7-tris(carboxymethyl)-1,4,7,10-tetraazacyclododecane 10 g (28.87 mmol) of 1,4,7-triscarboxymethyl-1,4,7,10-tetraazacyclododecane (=DO3A) and 12.99 g (51.96 mmol) of 2,3-epoxy-1-[4-(2-ethoxycarbonyl)-phenoxy]-propane are added in 80 ml of dioxane/60 ml of water and adjusted to pH 13 with 6N potassium hydroxide solution. It is stirred for 12 hours at room temperature. Then, it is refluxed for 2 hours. It is adjusted to pH 7 with 5N hydrochloric acid and evaporated to dryness in a vacuum. The residue is absorptively precipitated in 200 ml of ethanol/50 ml of chloroform at 60° C. The precipitated potassium chloride is filtered off and the filtrate is concentrated by evaporation in a vacuum. The residue is purified on a reversed-phase column (RP-18, washing with water, then elution with tetrahydrofuran/water=2:1). The main fractions are concentrated by evaporation in a vacuum.

Yield: 8.43 g (54% of theory) of a vitreous solid

Analysis (relative to the anhydrous substance): C 53.32 H 6.71N 10.36 Cld. C 53.29 H 6.81N 10.31 c) Gadolinium complex of 10-[2-hydroxy-3-(4-(carboxy)-phenoxy)-propyl]-1,4,7-tris(carboxymethyl)-1,4,7,10-tetraazacyclododecane (as sodium salt)

8.1 g (14.98 mmol) of the title compound of example 23b is dissolved in 70 ml of deionized water and 2.72 g (7.49 mmol) of gadolinium oxide is added. It is heated for 3 hours to 90° C. The cooled solution is stirred for one hour with 6 ml of weak acid ion exchanger (AMB 252c) at room temperature. It is filtered off from the exchanger. The filtrate is adjusted to pH 7.2 with 2N sodium hydroxide solution and freeze-dried.

Yield: 9.99 g (93% of theory) of a colorless, amorphous powder

Analysis (relative to the anhydrous substance): C 40.22 H 4.50N 7.82 Gd 21.94 Na 3.21 Cld. C 40.17 H 4.60N 7.76 Gd 21.88 Na 3.27

Example 24 a) 2,3-Epoxy-1-[4-(ethoxycarbonyl)-benzyloxy]-propane

Analogously to example 6b, 4-hydroxyphenylethyl-acetate was used instead of the title compound of example 6a.

Yield: 53% of theory of a colorless oil

Analysis (relative to the anhydrous substance): C 66.09 H 6.83 Cld. C 66.16 H 6.78 b) 10-[2-Hydroxy-3-(4-(carboxymethyl)-phenoxy)-propyl]-1,4,7-tris(carboxymethyl)-1,4,7,10-tetraazacyclododecane 10 g (28.87 mmol) of 1,4,7-triscarboxymethyl-1,4,7,10-tetraazacyclododecane (=DO3A) and 12.99 g (51.96 mmol)

of 2,3-epoxy-1-[4-(2-ethoxycarbonyl)-benzyloxy]-propane are added in 80 ml of dioxane/60 ml of water and adjusted to pH 13 with 6N potassium hydroxide solution. It is stirred for 12 hours at room temperature. Then, it is refluxed for 2 hours. It is adjusted to pH 7 with 5N hydrochloric acid and evaporated to dryness in a vacuum. The residue is absorptively precipitated in 200 ml of ethanol/50 ml of chloroform at 60° C. The precipitated potassium chloride is filtered off and the filtrate is concentrated by evaporation in a vacuum. The residue is purified on a reversed-phase column (RP-18, washing with water, then elution with tetrahydrofuran/water=2:1). The main fractions are concentrated by evaporation in a vacuum.

Yield: 8.17 g (51% of theory) of a vitreous solid

Analysis (relative to the anhydrous substance): C 54.14 H 6.91 N 10.10 C 54.09 H 6.98 N 10.02 c) Gadolinium complex of 10-[2-hydroxy-3-(4-(carboxymethyl)-phenoxy)-propyl]-1,4,7-tris(carboxymethyl)-1,4,7,10-tetraazacyclododecane (as sodium salt)

7.9 g (14.24 mmol) of the title compound of example 24b is dissolved in 80 ml of deionized water and 2.58 g (7.12 mmol) of gadolinium oxide is added. It is heated for 3 hours to 90° C. The cooled solution is stirred for one hour with 8 ml of weak acid ion exchanger (AMB 252c) at room temperature. It is filtered off from the exchanger. The filtrate is adjusted to pH 7.2 with 2N sodium hydroxide solution and freeze-dried.

Yield: 9.58 g (92% of theory) of a colorless, amorphous powder

Analysis (relative to the anhydrous substance): C 41.09 H 4.69 N 7.67 Gd 21.52 Na 3.15 Cld. C 41.02 H 4.74 N 7.61 Gd 21.47 Na 3.21

Example 25 bis-Palmitic acid ester of the gadolinium complex of 10-(1-hydroxymethyl-2,3-dihydroxypropyl)-1,4,7-tris(carboxymethyl)-1,4,7,10-tetraazacyclododecane 5 g (8.28 mmol) of the gadolinium complex of 10-(1-hydroxymethyl-2,3-dihydroxypropyl)-1,4,7-tris(carboxymethyl)-1,4,7,10-tetraazacyclododecane (see European application no. 91250081.6) is dissolved in 100 ml of dimethylformamide and 4.04 g (40 mmol) of triethylamine is added. Within 15 minutes, 6.83 g (24.83 mmol) of palmitic acid chloride is instilled. It is stirred for 2 days at room temperature. The solution is evaporated to dryness in a vacuum and the residue is chromatographed on RP-18 (reversed phase/mobile solvent: gradient water/acetonitrile).

Yield: After concentration by evaporation of the main fractions, 7.25 g (81% of theory) of a waxy solid is obtained.

Analysis (relative to the anhydrous substance): C 55.53 H 8.48 N 5.18 Gd 14.54 Cld. C 55.61 H 8.30 N 5.25 Gd 14.40

Example 26 a) 3-Hydroxy-tridec(12)ene

A solution of 16.83 g (100 mmol) of 10-undecenaldehyde in 30 ml of ether is instilled in an ethylmagnesium iodide solution (produced from 2.92 g (120 mmol of magnesium and 18.71 g (120 mmol) of ethyl iodide in 50 ml of ether) at 0° C. and then stirred for 5 hours at room temperature. 100 ml of water is carefully instilled and the aqueous phase is adjusted to pH 2 with 10% hydrochloric acid. The organic phase is separated and the aqueous phase is extracted twice with 40 ml of ether each. The combined organic phases are dried on magnesium sulfate and concentrated by evaporation in a vacuum. The remaining oil is chromatographed on silica gel (mobile solvent: hexane/ethyl acetate=20:1).

Yield: 16.86 g (85% of theory) of a colorless oil

Analysis (relative to the anhydrous substance): C 78.72 H 13.21 Cld. C 78.90 H 13.12 b) 3-Benzyloxy-tridec(12)ene 2.52 g (104.87 mmol) of sodium hydride is added to 16 g (80.67 mmol) of the title compound of example 26a in 200 ml of dimethylformamide and stirred for 2 hours at 50° C. It is cooled in an ice bath to 0° C. and 17.94 g (104.87 mmol) of benzyl bromide is added. Then, it is stirred overnight at room temperature. 800 ml of water is added and the solution is extracted twice with 200 ml of hexane. The combined organic phases are dried on magnesium sulfate and concentrated by evaporation in a vacuum.

Yield: 23.03 g (99% of theory) of a colorless oil

Analysis (relative to the anhydrous substance): C 83.27 H 11.18 Cld. C 83.15 H 11.25 c) 1,2-Epoxy-11-benzyloxy-tridecane 14.8 g (51.3 mmol) of the title compound of example 26b is dissolved in 100 ml of chloroform. At 0° C., 11.51 g (66.7 mmol) of m-chloroperoxybenzoic acid is added and then it is allowed to heat to room temperature. It is stirred for 24 hours at room temperature. The precipitated precipitate is filtered off and the filtrate is washed several times with conc. sodium carbonate solution. The organic phase is dried on magnesium sulfate and concentrated by evaporation in a vacuum. The residue is chromatographed on silica gel (mobile solvent: hexane/ethyl acetate 15:1).

Yield: 12.5 g (80% of theory) of a colorless oil

Analysis (relative to the anhydrous substance): C 78.90 H 10.59 Cld. C 78.77 H 10.65 d) 10-(2-Hydroxy-11-benzyloxy-tridecyl)-1,4,7-tris-carboxymethyl-1,4,7,10-tetraazacyclododecane Analogously to example 4a, the title compound of example 26c was used instead of the epoxide used in example 4a.

Yield: 59% of theory of a vitreous, hygroscopic solid

Analysis (relative to the anhydrous substance): C 62.74 H 8.98 N 8.61 Cld. C 62.58 H 8.81 N 8.75 e) Gadolinium complex of 10-(2-hydroxy-11-benzyloxy-tridecyl)-1,4,7-tris-carboxymethyl-1,4,7,10-tetraazacyclododecane Analogously to example 4b, the title compound of example 26d was used for complexing instead of the title compound of example 4a.

Yield: 96% of theory of a colorless, amorphous powder

Analysis (relative to the anhydrous substance): C 50.72 H 6.89 N 6.96 Cld. C 50.60 H 6.96 N 6.84

Example 27 a) 1-[(4-Benzyloxy)-phenoxy]-undec(10)ene 32.43 g (100 mmol) of the p-toluenesulfonic acid ester of 10-undecenol, 20.03 g (100 mmol) of 4-benzyloxy-phenol and 5.61 g (100 mmol) of finely powdered potassium hydroxide in 300 ml of toluene are stirred overnight at 70° C. It is cooled, 500 ml of 1N sodium hydroxide solution is added, and the organic phase is separated. The aqueous phase is extracted once with 100 ml of toluene, the combined organic phases are dried on magnesium sulfate and concentrated by evaporation in a vacuum. The residue is recrystallized from slightly hot methanol.

Yield: 26.44 g (75% of theory) of colorless flakes

Analysis (relative to the anhydrous substance): C 81.77 H 9.15 Cld. C 81.58 H 9.27 b) 1,2-Epoxy-11-[(4-benzyloxy)-phenoxy]-undecane

Analogously to example 26c, the title compound of example 27a is used for epoxidation instead of the title compound of example 26b.

Yield: 87% of theory of a crystalline solid (from methanol)

Analysis (relative to the anhydrous substance): C 78.22 H 8.75 Cld. C 78.05 H 8.87 c) 10-[2-Hydroxy-11-(4-benzyloxy-phenoxy)-undecyl]-1,4,7-triscarboxymethyl-1,4,7,10-tetraazacyclododecane Analogously to example 4a, the title compound of example 27b was used instead of the epoxide used in example 4a.

Yield: 69% of theory of a vitreous solid

Analysis (relative to the anhydrous substance): C 63.84 H 8.18N 7.84Cld. C 63.67 H 8.31N 7.60 d) Gadolinium complex of 10-[2-hydroxy-11-(4-benzyloxy-phenoxy)-undecyl]-1,4,7-triscarboxymethyl-1,4,7,10-tetraazacyclododecane Analogously to example 4b, the title compound of example 27c was used for complexing instead of the title compound of example 4a.

Yield: 98% of theory of a colorless crystalline powder

Analysis (relative to the anhydrous substance): C 52.51 H 6.38N 6.45Gd 18.09 Cld. C 52.32 H 6.45N 6.28Gd 17.91

Example 28

10-[2-Hydroxy-11-(4-hydroxy-phenoxy)-undecyl]-1,4,7-triscarboxymethyl-1,4,7,10-tetraazacyclododecane Analogously to example 7, the title compound of example 27d was hydrogenated.

Yield: 97% of theory of a vitreous solid

Analysis (relative to the anhydrous substance): C 47.80 H 6.34N 7.19 Gd 20.19 Cld. C 47.61 H 6.50N 7.02 Gd 20.03

Examples for the form of administration 1. 372.42 g (0.5 mmol) of the complex salt described in example 21c is dissolved with heating in 500 ml of water pro injectione (p.i). After adding 1.2 g of tromethamine, the neutral solution is filled with water p.i. to 1000 ml. The solution is ultrafiltered and bottled in flasks. After heat sterilization, it is ready for parenteral administration.

2. 128 g (0.19 mol) of the complex described in example 14b is intensively mixed with 120 g of saccharose and 5 g of polyoxyethylene polyoxypropylene while adding 10 mg of raspberry aromatic substance. The resulting powder is used for oral administration.

| $T_1$-Relaxivities (in plasma) of several selected examples | |
|---|---|
| Example No. | $T_1$-Relaxivity $(mM \cdot s)^{-1}$* |
| 1b | 7.30 |
| 2b | 7.27 |
| 3b | 7.16 |
| 4b | 24.47 |
| 5c | 12.18 |
| 6d | 24.16 |
| 7 | 9.91 |
| 8b | 5.76 |
| 11b | 8.66 |
| 12b | 10.23 |
| 13b | 8.70 |
| 14b | 7.25 |
| 21c | 7.28 |
| 23c | 7.04 |
| Magnevist ® | 4.90 |
| Dotarem ® | 4.30 |

*The $T_1$-relaxivity was measured in human plasma with a NMR pulse spectrometer (Minispec PC 20) at 20 Mhz (= 0.47 T) and 39° C.

Example for an in vivo NMR diagnosis

The experimental animals (rats, Wistar Han, with novikoff hepatoma in the liver) are anesthetized (Rompun®+ Ketavel®) for the nuclear spin tomographic test and provided with a catheter in the caudal vein for the administration of the contrast medium. The test takes place in an MRI experimental device of the General Electric company (field strength 2 teslas). The images are made with a $T_1$-weighted spin echo sequence (TR=400 m sec, TE=20 m sec, 8 averages of a 3 mm layer thickness, axial type of incision). An image of the liver with the tumor before the administration of shows that the tumor is more or less isodense with the liver parenchyma and cannot be differentiated from the latter. One minute after i.v. administration of the title compound of example 14b (0.1 mmol of Gd/kg), the liver exhibits an increased signal intensity, while the signal intensity of the tumor (upper right) has not changed, so that both are now very easy to differentiate from one another. Also, 30 minutes after administration, the contrast between liver and tumor is still completely maintained. This means that this substance is concentrated in the liver in contrast to commercial preparations Magnevist® and Dotarem® and as a result, in comparison to the latter in the same dosage, first produces a considerably better contrast between liver parenchyma and tumor (and also other pathological phenomena) and second, preserves this contrast for a longer period. Finally, it is advantageous, since thus a greater period of time is available for a successful diagnosis.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A tetraazacyclododecane compound of the formula I (I)

in which

E stands for radical —CH(R$^1$)—CO$_2$Y with each Y independently meaning a hydrogen atom or a metal ion equivalent of an element of atomic numbers 21–29, 31, 32, 37–39, 42–44, 47, 49 or 57–83 and R$^1$ meaning a hydrogen atom, a branched or unbranched C$_1$–C$_{30}$ alkyl, C$_6$–C$_{10}$ aryl or C$_7$–C$_{30}$ aralkyl group, each optionally substituted with 1 to 6 hydroxy groups, Q stands for a radical —CH(R')—CH(OH)R with R meaning a branched or unbranched $C_1$–$C_9$ saturated carbon chain or $C_1$–$C_6$ saturated carbon chain containing at least one aryl radical, each carbon chain containing 1 to 10 oxa atoms and optionally substituted by 1 to 6 hydroxy or —OCOR$^2$ groups, with R$^2$ meaning a hydrogen atom or a branched or unbranched $C_1$–$C_9$ alkyl, $C_6$–$C_{10}$ aryl or $C_7$–$C_{30}$ aralkyl radical, wherein R optionally is substituted by 1 to 2 —CO$_2$R$_2$, 1 to 2 —OCO— groups, 1 to 2 cyclohexane and/or cyclohexylene radicals, each of which can be substituted by 1 to 3 (CH$_2$)$_k$COOR$^2$ groups with k meaning the numbers 0 to 10, 1 to 5 $C_1$–$C_7$ alkoxy, $C_6$–$C_{10}$ aryloxy or $C_7$–$C_{10}$ aralkyloxy groups, and/or a radical —NR$^2$—COR$^3$ or —CONR$^2$R$^3$, wherein R$^3$ has one of the meanings indicated for R$^2$, and wherein the aryl radicals optionally contained in the chain can be substituted by 1 to 3 branched or unbranched $C_1$–$C_{30}$-alkyl, $C_6$–$C_{10}$-aryl or $C_7$–$C_{30}$-aralkyl radicals, each alkyl chain optionally substituted by 1 to 5 oxa atoms and each alkyl chain or aryl ring optionally substituted by 1 to 3 hydroxy radicals, 1 to 5 $C_1$–$C_7$ alkoxy groups and/or 1 to 3 (CH$_2$)$_k$COOR$^2$ groups, and/or by 1 to 3 F, Cl, Br, OH, NO$_2$, NH$_2$, NCS, CO$_2$R$^2$, NHCOCH$_2$Cl, NHCOCH$_2$Br, NHCOCH$_2$R$^2$, or CON$_3$ radicals, and R' meaning a hydrogen atom or an R group, in which, if R' stands for a hydrogen atom, in the case of 2-oxa-$C_1$–$C_{30}$ alkyl chain, the latter, in addition to an optionally present, terminal methoxy or ethoxy group, has to be substituted by at least one of the above-identified radicals, or a salt thereof with an inorganic and/or organic base, amino acid or amino acid amide;

provided that R does not terminate in a linear alkoxy group.

2. The compound of claim 1, wherein each R$^1$ stands for a hydrogen atom.

3. The compound of claim 1, wherein, in the compound of Formula I, R is —CH$_2$—O—C$_6$H$_5$, —CH$_2$—O—CH$_2$C$_6$H$_5$, —CH$_2$—O—C$_{10}$H$_{20}$—OH, —CH$_2$—O—C$_{10}$H$_{20}$—COOH, —CH$_2$—O—C$_5$H$_{10}$—COOH, —CH$_2$—CH$_2$—CH$_2$—CH$_2$—O—CH$_2$—COOH, —CH$_2$—O—C$_6$H$_{10}$—CO$_2$H, —CH$_2$—O—C$_6$H$_{10}$—OH, —C$_6$H$_{10}$—O—CH$_2$—COOH, —CH$_2$—O—C$_5$H$_{10}$NHCOC$_6$H$_5$, —CH$_2$—O—C$_2$H$_5$NHCOC$_6$H$_5$, —CH$_2$—O—C$_2$H$_5$CONH—C$_3$H$_7$, —CH$_2$—O—CH$_2$—CH(OH)CH$_2$OH, —CH$_2$—O—C$_6$H$_4$NCS, —CH$_2$—O—C$_6$H$_4$—COOH, —CH$_2$O—C$_6$H$_4$—C$_5$H$_{10}$, —OH, —CH$_2$—O—C$_6$H$_3$(CH$_3$)$_2$, —CH$_2$—O—C$_6$H$_4$(CH$_2$)$_2$—COOH, —CH$_2$—O—C$_6$H$_4$—OCH$_2$COOH, —CH$_2$—O—C$_6$H$_4$COOH, —CH$_2$O—CH$_2$—C$_6$H$_4$COOH, —CH$_2$O—C$_6$H$_4$CH$_2$COOH, —CH$_2$O—C$_6$H$_4$CH$_2$COOC$_2$H$_5$, —(CH$_2$)$_9$—O—CH$_2$—C$_6$H$_5$, —CH$_2$—OCO—C$_{15}$H$_{31}$, —CH$_2$—O—C$_9$H$_{18}$—O—CH$_2$C$_6$H$_5$, —CH$_2$—O—C$_9$H$_{18}$OH, —C$_8$H$_{16}$—(CH$_2$—O—CH$_2$—C$_6$H$_5$)—C$_2$H$_5$, —C$_9$H$_{18}$—O—C$_6$H$_4$—O—CH$_2$—C$_6$H$_5$, —C$_9$H$_{18}$—O—C$_6$H$_4$—OH, —(CH$_2$)$_9$—O—CH$_2$—C$_6$H$_4$—CH$_2$COOH, —(CH$_2$)$_9$—O—C$_{10}$H$_{20}$—OH, —(CH$_2$)$_9$—O—C$_5$H$_{10}$—COOH, —(CH$_2$)$_9$—OCOCH$_3$, —(CH$_2$)$_9$—OCOC$_4$H$_9$—(CH$_2$)$_9$, —OCOC$_2$H$_4$COOH, —(CH$_2$)$_9$—OCOC$_6$H$_4$COOH or —(CH$_2$)$_9$—OCOC$_6$H$_{10}$COOH.

4. A compound according to claim 1, wherein each Y stands for a hydrogen atom.

5. A compound according to claim 1, wherein at least two of the substituents Y are metal ion equivalents of at least one element of atomic numbers 21–29, 42, 44 or 57–83 or at least one radionuclide of an element of atomic numbers 21, 26, 27, 29, 31, 32, 37–39, 43, 47, 49, 62–64, 67, 70, 71, 75, 77, 79 and 83.

6. A compound according to claim 1, wherein R' stands for a hydrogen atom.

7. A pharmaceutical composition comprising a physiologically compatible compound according to claim 1 and a pharmaceutical carrier.

8. The compound of claim 1, wherein R contains at least one aryl radical substituted with at least one NO$_2$, NH$_2$, NCS, NHCOCH$_2$Cl, NHCOCH$_2$Br, NHCOCH$_2$R$^2$, or CON$_3$ radical substituent.

9. The compound of claim 1, wherein Q is 3-(4-nitrophenoxy)-2-hydroxypropyl.

10. The compound of claim 1, wherein Q is 2,6,7-trihydroxy-4-oxaheptyl.

11. The compound of claim 1, wherein at least two Y substituents are metal ion equivalents of an element of atomic number 21–29, 42, 44 or 58–70.

12. The compound of claim 1, wherein Q is 3-(4-aminophenoxy)-2-hydroxypropyl.

13. The compound of claim 1, wherein Q is 3-(4-isothiocyanatophenoxy)-2-hydroxypropyl.

14. The compound of claim 1, wherein Q is 3-(4-carboxyphenoxy)-2-hydroxypropyl.

* * * * *